US010335043B2

(12) United States Patent
Jain et al.

(10) Patent No.: US 10,335,043 B2
(45) Date of Patent: Jul. 2, 2019

(54) IMPLANTABLE VITAL SIGN SENSOR

(71) Applicant: Thomas Jefferson University, Philadelphia, PA (US)

(72) Inventors: Apurva Jain, Philadelphia, PA (US); Jeffrey I. Joseph, Penn Valley, PA (US); Nance Dicciani, Fort Washington, PA (US); Denise Devine, Media, PA (US); David Demmer, Toronto (CA)

(73) Assignee: Thomas Jefferson University, Philadelphia, PA (US)

( * ) Notice: Subject to any disclaimer, the term of this patent is extended or adjusted under 35 U.S.C. 154(b) by 330 days.

(21) Appl. No.: 15/354,623

(22) Filed: Nov. 17, 2016

(65) Prior Publication Data

US 2017/0065188 A1    Mar. 9, 2017

Related U.S. Application Data

(63) Continuation-in-part of application No. 15/083,676, filed on Mar. 29, 2016.
(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0006* (2013.01); *A61B 5/0031* (2013.01);
(Continued)

(58) Field of Classification Search
None
See application file for complete search history.

(56) References Cited

U.S. PATENT DOCUMENTS 3,049,001 A    8/1962  Mackay et al.
5,749,367 A    5/1998  Gamlyn et al.
(Continued)

FOREIGN PATENT DOCUMENTS

WO         9829030      7/1998
WO     2004014456 A2    2/2004
(Continued)

OTHER PUBLICATIONS

International Search Report and Written Opinion dated May 30, 2016 for International Application No. PCT/US2016/024655, International Filing Date Mar. 29, 2016 consisting of 14 pages.
(Continued)

*Primary Examiner* — Eric F Winakur
*Assistant Examiner* — Marjan Fardanesh
(74) *Attorney, Agent, or Firm* — Christopher & Weisberg, P.A.

(57) ABSTRACT

An implantable vital sign sensor including a housing including a first portion, the first portion defining a first open end, a second open end opposite the first end, and a lumen there through, the first portion being sized to be implanted substantially entirely within the blood vessel wall of the patient. A sensor module configured to measure a blood vessel blood pressure waveform is included, the sensor module having a proximal portion and a distal portion, the distal portion being insertable within the lumen and the proximal portion extending outward from the first open end.

1 Claim, 11 Drawing Sheets

Related U.S. Application Data

(60) Provisional application No. 62/256,476, filed on Nov. 17, 2015, provisional application No. 62/168,754, filed on May 30, 2015, provisional application No. 62/143,592, filed on Apr. 6, 2015.

(51) Int. Cl.
  A61B 5/024 (2006.01)
  A61B 5/145 (2006.01)
  A61B 5/0215 (2006.01)
  A61B 5/1455 (2006.01)
  A61B 5/08 (2006.01)

(52) U.S. Cl.
  CPC ........ A61B 5/0215 (2013.01); A61B 5/02416 (2013.01); A61B 5/0816 (2013.01); A61B 5/14542 (2013.01); A61B 5/14551 (2013.01); A61B 5/686 (2013.01); A61B 5/6876 (2013.01); A61B 5/6879 (2013.01); A61B 2562/0247 (2013.01); A61B 2562/0271 (2013.01); A61B 2562/063 (2013.01)

(56) References Cited

U.S. PATENT DOCUMENTS

| | | | |
|---|---|---|---|
| 5,995,860 A | 11/1999 | Sun et al. | |
| 6,049,727 A | 4/2000 | Crothall | |
| 6,122,536 A | 9/2000 | Sun et al. | |
| 6,743,180 B1 | 6/2004 | Van Bockel | |
| 6,999,810 B2 | 2/2006 | Bemer et al. | |
| 7,011,630 B2 | 3/2006 | Desai et al. | |
| 7,018,568 B2 | 3/2006 | Tierney | |
| 7,024,236 B2 | 4/2006 | Ford et al. | |
| 7,044,920 B2 | 5/2006 | Letort | |
| 7,150,975 B2 | 12/2006 | Tamada et al. | |
| 7,163,511 B2 | 1/2007 | Conn et al. | |
| 7,174,199 B2 | 2/2007 | Berner et al. | |
| 7,295,867 B2 | 11/2007 | Bemer et al. | |
| 7,405,055 B2 | 7/2008 | Dunn et al. | |
| 7,450,999 B1 | 11/2008 | Karicherla et al. | |
| 7,519,478 B2 | 4/2009 | Bartkowiak et al. | |
| 7,521,019 B2 | 4/2009 | Polak et al. | |
| 7,523,004 B2 | 4/2009 | Bartkowiak et al. | |
| 7,604,593 B2 | 10/2009 | Parris et al. | |
| 7,647,831 B2 | 1/2010 | Corcoran et al. | |
| 7,699,775 B2 | 4/2010 | Desai et al. | |
| 7,711,493 B2 | 5/2010 | Bartkowiak et al. | |
| 7,731,867 B2 | 6/2010 | Li et al. | |
| 7,818,131 B2 | 10/2010 | Mott | |
| 7,873,399 B2 | 1/2011 | Bemer et al. | |
| 7,935,499 B2 | 5/2011 | Dunn et al. | |
| 7,966,886 B2 | 6/2011 | Corcoran et al. | |
| 7,991,625 B2 | 8/2011 | Rosenfeld et al. | |
| 8,597,185 B2 | 12/2013 | Pipke | |
| 8,600,777 B2 | 12/2013 | Schoenberg et al. | |
| 8,602,999 B2 | 12/2013 | Young et al. | |
| 8,620,591 B2 | 12/2013 | Wegerich | |
| 2003/0069752 A1 | 4/2003 | LeDain et al. | |
| 2004/0152999 A1 | 8/2004 | Cohen et al. | |
| 2005/0288596 A1 | 12/2005 | Eigler et al. | |
| 2006/0178583 A1 | 8/2006 | Montegrande et al. | |
| 2007/0163353 A1 | 7/2007 | Lee et al. | |
| 2009/0093729 A1 | 4/2009 | Zhang et al. | |
| 2011/0124982 A1 | 5/2011 | Pipke | |
| 2011/0144967 A1 | 6/2011 | Adirovich | |
| 2013/0247644 A1 | 9/2013 | Swoboda et al. | |
| 2014/0163392 A1* | 6/2014 | Flanders | A61B 5/6852 600/480 |

FOREIGN PATENT DOCUMENTS

| | | |
|---|---|---|
| WO | 2007010391 A1 | 1/2007 |
| WO | 2013173747 A1 | 11/2013 |

OTHER PUBLICATIONS

Penc Cong et al.: "Wireless Batteryless Implantable Blood Pressure Monitoring Microsystem for Small Laboratory Animals", Article, Feb. 2010, vol. 10, No. 2, IEEE Sensors Journal, pp. 243-254, consisting of 12 pages.

Anna G.C.D. Ribeiro et al.: "Wireless Monitoring of Patient's Vital Signs", Laboratory of Hospital Automation and Bioengineering, Federal University of Rio Grande do Norte, State University of Rio Grande do Norte, Brazil, consisting of 21 pages.

Nuria Oliver et al.: "HealthGear: A Real-time Wearable System for Monitoring and Analyzing Physiological Signals", 2006 IEEE Computer Society, pp. 1-4, consisting of 4 pages.

James Xin Sun, Cardiac Output Estimation using Arterial Blood Pressure Waveforms, Massachusetts Institute of Technology, Sep. 2006, 7 pages.

FDA Executive Summary, CardioMEMS Champion HF Monitoring System CardioMEMS, Inc., Prepared for the Oct. 9, 2013 meeting of the Circulatory Systems Devices Panel, P100045/A004, 52 pages.

Lawrence Yu et al., Chronically Implanted Pressure Sensors: Challenges and State of the Field, Sensors 2014, 14, 20620-20644; doi:10.3390/s141120620.

Olive H. Murphy et al., Continuous in vivo blood pressure measurements using a fully implantable wireless SAW sensor, Biomed Microdevices (2013) 15:737-749, DOI 10.1007/s10544-013-9759-7.

Malcom Elliott and Alysia Coventry, Critical care: the eight vital signs of patient monitoring, British Journal of Nursing, 2012, vol. 21, No. 10, 5 pages.

Robert Tan et al., Development of a fully implantable wireless pressure monitoring system, Biomed Microdevices (2009)11:259-264, DOI 10.1007/s10544-008-9232-1.

Jay Ritzema et al., Direct Left Atrial Pressure Monitoring in Ambulatory Heart Failure Patients: Initial Experience With a New Permanent Implantable Device, Circulation. 2007;116:2952-2959; originally published online Dec. 3, 2007; doi: 10.1161/CIRCULATIONAHA.107.702191.

Dr. Lazar Mathew, EE 625: Bio Sensors and BioMEMS, Sujay B. Desai: Roll # 08D07033, 6 pages.

H. Fassbender et al., Fully implantable blood pressure sensor for hypertonic patients, IEEE Sensors 2008 Conference, 4 pages.

Eric Y. Chow et al., Fully Wireless Implantable Cardiovascular Pressure Monitor Integrated with a Medical Stent, IEEE Transactions on Biomedical Engineering, vol. 57, No. 6. Jun. 2010, 10 pages.

P. Bingger et al., Highly Flexible capacitive strain gauge for continuous long-term blood pressure monitoring, Biomed Microdevices (2012) 14:573-581 DOI 10.1007/s10544-012-9636-9.

Chih-Wen Cheng, icuARM—An ICU Clincial Decision Support System Using Association Rule Mining, 10.1109/JTEHM.2013. 2290113, IEEE Journal of Translational Engineering in Health and Medicine, 10 pages.

Marek Swoboda, Implantable Arterial Blood Pressure Sensor, A Thesis Submitted to the Faculty of Drexel University in partial fulfillment of the requirements for the degree of Doctor of Philosophy, Dec. 2004, 245 pages.

Faisal M. Merchant et al., Implantable Sensors for Heart Failure, (Circ Arrhyth Electrophysiol. 2010;3:657-667), DOI: 10.1161/CIRCEP.110.959502.

Faisal M. Merchant et al., Implantable Sensors for Heart Failure, Circulation Arrhythmia and Electrophysiology, 2010;3:657-667, doi: 10.1161/CIRCEP.110.959502.

Joseph A. Potkay, Long term, implantable blood pressure monitoring systems, Biomed Microdevices (2008) 10:379-392, DOI 10.1007/s10544-007-9146-3.

Wolf W. Von Maltzahn, Medical Instruments and Devices VIII, University of Texas at Arlington, 237 pages.

Nader Najafi et al., MEMS implant for cardiovascular applications, MICRO NANO, The Newsletter of Tools adn Products in Micro and Nanotechnology, Sep. 2009, vol. 8, No. 9, 1 page.

(56) References Cited

OTHER PUBLICATIONS

MEMS Pressure Sensor Solutions, NOVA Sensor, AAS-BR-212C-05/2015, 8 pages.
A. Vasudev, Microelectromechanical systems (MEMS) for in vivo applications, DOI: 10.1533/9780857096289.3331, 13 pages.
Pinet E. et al., Miniature Fiber Optic Pressure Sensor for Medical Applications: an Opportunity for Intra-Aortic Balloon Pumping (IABP) therapy, Abstract, 4 pages.
Lionsgate Technologies Inc., Mobile Vital Signs Monitoring: Everyone, Everywhere, A Technology Whitepaper by LionsGate Technologies Inc., Mar. 2013, 5 pages, info@LDTmedical.com, www.LGTmedical.com.
U. Kyriacos et al., Monitoring vital signs using early warning scoring systems: a review of the literature, Journal of Nursing Management, 2011, 19, 311-330.
Peng Cong et al., Novel Long-Term Implantable Blood Pressure Monitoring System with Reduced Baseline Drift, Proceedings of the 28th IEEE, EMBS Annual International Conference, New York City, USA, Aug. 30-Sep. 3, 2006, 4 pages.
Sim JJ., Overtreatment, undertreatment of hypertension raises risk for mortality and renal disease, Cardiology today, Am Coll Cardiol. 2014;64:588-59, Aug. 6, 2014.
U.S. Department of Health and Human Services, Prevention, Detection, Evaluation, and Treatment of High Blood Pressure, National Institutes of Health, National Heart, Lung, and Blood Institute, 104 pages.
MD+DI Staff, Promising Cardio Technologies, Heart disease kills one in four people in the United States, but these breakthrough technologies are aiming to change that, MedTechWorld, Jan. 2016, 6 pages.
ISA, Remote Vital Signs Monitoring, Project Report Version 1.0, Emeline Alves Goncalves—Nr. 501022516, Sep. 10, 2007, Physics Department, Faculty of Sciences and Technology, University of Coimbra, 104 pages.
American Heart Association, Selecting the Most Appropriate Blood Pressure Measurement Method for Preclinical Research: AHA Recommendations Then and Now, 4 pages.
David M. Cutler, The Value of Antihypertensive Drugs: A Perspective on Medical Innovation, Health Affairs—vol. 26, No. 1, (2007): 97-110, DOI 10.1377/hlthaff.26.1.97.
Baozhi Chen & Dario Pompili, Transmission of Patient Vital Signs Using Wireless Body Area Networks, Mobile Netw Appl, DOI 10.1007/s11036-010-0253-7, 20 pages.
Jason W.P. NG et al., Ubiquitous Monitoring Environment for Wearable and Implantable Sensors (UbiMon), Imperial College London, 180 Queen's Gate, London SW7 2AZ, UK, 2 pages.
Armand Pruijmboom, VCSEL-based miniature laser-Doppler interferometer, Proc. Of SPIE vol. 6908 690801-1, 7 pages.
Tia Gao, Vital Signs Monitoring and Patient Tracking Over a Wireless Network, Johns Hopkins University Applied Physics Laboratory, In Proceedings of the 27th Annual International Conference of the IEEE EMBS, Shanghai, Sep. 2005, 4 pages.
Ron Wilson, Watch for Small Warnings Before a Cardiac Arrest, Wall Street Journal, D1-D2, Tuesday, Feb. 2, 2016, 2 pages.
Dr. Mehran Mehregany, Wireless health to drive a trillion sensors, evaluationengineering.com, Mar. 2016, 3 pages.
John S. Ho et al., Wireless power transfer to deep tissue microimplants, 7974-7979, PNAS, Jun. 3, 2014, vol. 111, No. 22.

\* cited by examiner

IMPLANTABLE VITAL SIGN SENSOR

CROSS-REFERENCE TO RELATED APPLICATION

This application is a Continuation-in-Part application of U.S. patent application Ser. No. 15/083,676, filed Mar. 29, 2016 entitled "IMPLANTABLE VITAL SIGN SENSOR", which is related to and claims priority to U.S. Provisional Patent Application Ser. No. 62/143,592, filed Apr. 6, 2015, entitled "IMPLANTABLE VITAL SIGN SENSOR", and is also related to and claims priority to U.S. Provisional Patent Application Ser. No. 62/168,754, filed May 30, 2015, entitled "IMPLANTABLE VITAL SIGN SENSOR", and is also related to and claims priority to U.S. Provisional Application Ser. No. 62/256,476, file Nov. 17, 2015, entitled "OPTICAL METHODS FOR MEASURING PRESSURE LONG TERM TO DETECT AND MONITOR PRESSURE VARIATIONS AND WAVEFORMS", the entire contents of each are hereby incorporated herein by reference.

STATEMENT REGARDING FEDERALLY SPONSORED RESEARCH OR DEVELOPMENT n/a

FIELD

An implantable vital signs sensor and method of implantation thereof.

BACKGROUND

Real-time monitoring of a non-ambulatory patient's vital signs is typically achieved through non-invasive methods. For example, a patient in an operating room or ICU bed may have a blood pressure monitor with a cuff disposable about the upper arm; a pulse oximeter engaged around a fingertip; adhesive electrodes affixed to the skin (proximate to the heart) that measure the electrocardiogram and respiratory rate/pattern of respiration; an oral/aural thermometer that measures body temperature, and a stethoscope for monitoring heart/lung/airway sounds. These non-invasive vital signs sensors are often cumbersome and unwieldy. Patients that are hospitalized, immobilized, or stationary commonly tolerate the inconveniences inherent in non-invasive sensors. Continuous monitoring of hospitalized patients in the emergency room, operating room, intensive care unit, and catheterization laboratory may help medical professionals detect clinically significant changes in patient physiology. Vital sign trend data may be used to monitor and adjust medical and surgical therapy which may lead to decreased morbidity and mortality. Ambulatory patients may use telemedicine software programs to intermittently communicate with medical professionals at a remote location, using a computer program like Skype. A brief period of vital sign trend data may be transmitted via the internet to a central monitoring station for clinician interpretation. Intermittent home telemedicine has been successfully used to manage patients with conditions such as congestive heart failure, type 2 diabetes, influenza and premature labor outside of the emergency room and hospital.

A medical professional may order short-term recording of an ambulatory patient's vital sign data using non-invasive sensors for several days, weeks or months. The recorded trend data may be downloaded to a computer and interpreted to determine the clinical significance. The real-time monitoring of an ambulatory patient's vital signs, however, is more challenging owing to the patient's mobility, and lack of supervision by hospital staff. Many patients are not compliant obtaining frequent or timely vital sign measurement using non-invasive sensors. Moreover, even when a patient is attentive to compliance, the cumbersome nature of such devices often results in patient's either removing the devices or shifting the devices to a more comfortable position, which can create artifacts, inaccurate readings, and occlude blood flow. Moreover, non-invasive devices are typically less accurate and less stable than implantable sensors.

Short-term and long-term implantable intravascular blood pressure sensors have been devised to measure blood pressure in real-time. Catheters are sometimes inserted short-term into the peripheral artery of a patient to monitor arterial blood pressure and arterial pressure waveform. Long-term intravascular blood pressure sensors may be inserted into the bloodstream of large arteries and veins to chronically monitor research animals. However, such intravascular blood pressure sensors are prone to obstruct blood flow and cause endothelial cell injury, thrombosis, and emboli. Other long-term implantable blood pressure sensors are disposed around the outer diameter of an artery wall and use application to produce a robust mechanical coupling with the transducer's diaphragm.

SUMMARY

An implantable vital sign sensor including a housing including a first portion, the first portion defining a first open end, a second open end opposite the first end, and a lumen there through, the first portion being sized to be implanted substantially entirely within the blood vessel wall of the patient. A sensor module configured to measure a blood vessel blood pressure waveform is included, the sensor module having a proximal portion and a distal portion, the distal portion being insertable within the lumen and the proximal portion extending outward from the first open end.

In another embodiment, a method of implanting a vital sign sensor includes making an incision in the skin and advancing a blood vessel piercing element. The blood vessel wall is pierced with the blood vessel piercing element and the blood vessel piercing element is advanced through the vessel wall tissue to create a cavity therein. A housing is slid over the blood vessel piercing element and positioned within the cavity, the housing defines a lumen there though, with the distal end of the housing disposed proximate to the endothelial cells and their basement membrane. A sensor module may be inserted within the lumen of the housing until the sensor's diaphragm is disposed adjacent to the endothelial cells and their basement membrane, the sensor module being configured to measure a blood vessel blood pressure waveform.

In yet another embodiment, the implantable vital sign sensor includes an elongate and biodegradable housing including a first portion, the first portion defining a first open end, a second open end opposite the first end, and a lumen there through, the first portion being sized to be implanted substantially entirely within the arterial wall of the patient. A second portion is substantially orthogonal with the first portion and configured to contour an exterior surface of the arterial wall when the distal end of the first portion is inserted to a position within the arterial wall substantially co-planar to the basement membrane and endothelial cells of the arterial wall. A sensor module retainable within the first portion is included, the sensor module having a pressure transducer configured to measure an arterial blood pressure waveform, the sensor module having a deflectable diaphragm responsive to a blood pressure waveform within the artery, the diaphragm being substantially co-planar to the basement membrane and endothelial cells of the arterial wall when the sensor module is retained within the first portion. The housing may be constructed from a biocompatible material that is permanent or a material that degrades days to months after being implanted in the body.

BRIEF DESCRIPTION OF THE DRAWINGS

A more complete understanding of the present invention, and the attendant advantages and features thereof, may be more readily understood by reference to the following detailed description when considered in conjunction with the accompanying drawings wherein.

DETAILED DESCRIPTION

Figure 1:
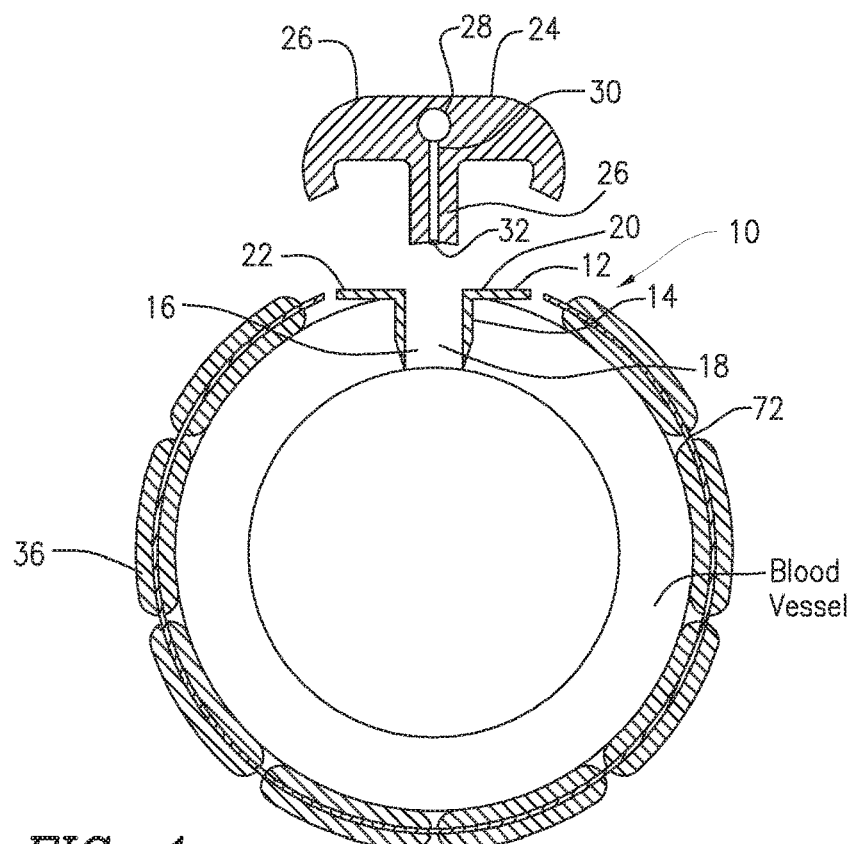
FIG. 1 is a front cross-sectional view of an embodiment of implantable sensor constructed in accordance with the principles of the present invention.

As used herein, relational terms, such as "first" and "second," "over" and "under," "front" and "rear," "in, within, and around" and the like, may be used solely to distinguish one entity or element from another entity or element without necessarily requiring or implying any physical or logical relationship or order between such entities or elements.

Referring now to the drawings in which like reference designators refer to like elements, there is shown in FIGS. 1-5 an exemplary implantable vital signs sensor device and monitoring system constructed in accordance with the principles of the present application and designated generally as "10." As used herein the phrase "vital signs" refers to measurements related to a patient's, whether human or animal, basic body functions, including but not limited to, heart rate, blood pressure, blood pressure waveform, blood flow, respiratory rate, tidal volume, electrocardiogram, temperature, hemoglobin oxygen saturation, body position, activity level, and related measurements. The device 10 may include a housing 12 sized to be at least substantially retained entirely within a blood vessel wall of a patient, and in particular, the wall of a vein or an artery.

The long-term implantable vital sign monitoring device 10 may monitor one or more of the following physiologic parameters in real-time to determine a significant change from an individual patient's baseline pattern when living in the real-world environment: heart rate, heart rhythm, stroke volume, blood pressure, systemic vascular resistance, blood flow, myocardial contractility, valve function, cardiac timing intervals, respiratory rate, respiratory rhythm, tidal volume, hemoglobin oxygen saturation, heart sounds, lung sounds, upper airway sounds, bowel sounds, temperature, electrocardiogram (lead 2, V2, and V5), activity level, body position, and location on the earth. The long-term implantable vital sign monitoring device 10 may also record and store in memory one or more of the parameters for subsequent interpretation.

For example, the housing 12 may be sized to span the wall thickness of at least one of the internal thoracic (mammary) artery lateral thoracic artery, subscapular artery, intercostal artery, superior epigastric artery, carotid artery, aorta, renal artery, iliac artery, femoral artery, brachial artery, ulnar artery, and radial artery, which may range in wall thickness between approximately 100-1500 microns. For example, the housing 12 may be sized to span the wall thickness of at least one of the internal thoracic vein, lateral thoracic vein, internal jugular vein, external jugular vein, renal vein, vena cava, axillary vein, brachial vein, iliac vein, femoral vein and a peripheral vein, which may range in wall thickness between approximately 40-1000 microns. In addition, the housing 12 may be sized to span the wall thickness of a pulmonary artery or a pulmonary vein, which may range in wall thickness between approximately 40-1000 microns. The housing 12 may be composed of biodegradable and biocompatible materials such as polymers, biopolymers, hydrogels, collagen, elastin, hyaluronic acid and polylactic acid, such that it may degrade after a predetermined amount of time within the body. Alternatively, the housing 12 may be composed of a biocompatible material such as stainless steel, titanium, composite, ceramic, silicone, PTFE, PE, PVC, epoxy, or glass that does not degrade over time. The housing 12 may be smooth or textured and coated with one or more compounds that promote the adhesion and health of the vessel wall tissue.

The housing 12 may include a first portion 14 sized to substantially span the entirety of wall thickness of the artery or vein into which the housing 12 is implanted. The first portion 14 may be substantially cylindrical in shape and define a lumen 16 there through. For example, when inserted within the internal mammary (thoracic) artery, the first portion 14 may define a length of approximately between 200-1,500 microns and a surface area of approximately 1 mm². In other configurations, the first portion 14 may define any hollow structure sized to substantially span the arterial wall thickness and provide the lumen 16 there through. The first portion 14 may further define a smooth outer surface to facilitate placement within the artery wall tissue, or alternately, may be threaded on its outer surface such that the first portion 14 may be secured within the artery wall tissue through rotation of the first portion 14. The first portion 14 may be adhered within the arterial wall with an adhesive, or alternatively, may include a textured surface that promotes the adhesion, ingrowth, or attachment of the surrounding vessel wall tissue or barbs or tines that engage the surrounding tissue. The first portion 14 further includes an open first end 18 configured to be positioned immediately adjacent to the basement membrane and endothelial cells of the artery (tunica intima) such that the first open end 18 is not in contact with blood flowing within the artery or vein and a second open end 20 opposite the first end 18. In an exemplary configuration, the distance between the first open end 18 and the blood stream when the first portion 14 is implanted within the arterial wall may be approximately 5 to 200 microns. In another configuration, the first open end 18 is substantially co-planar with the basement membrane and endothelial cells. In another configuration, the first end can extend 5 to 200 micrometers into the artery lumen, in contact with the flowing blood. In another configuration, the first end 18 may extend into the artery lumen, in contact with flowing blood.

Attached to the second end 20 may be a second portion 22 of the housing 12. The second portion 22 may be positioned substantially orthogonal to the first portion 14 and may extend across and contour at least a portion of the outer diameter of the arterial wall. For example, the second portion 22 may be substantially flat, rectangular, or round in shape, or alternatively, may define a curvature substantially corresponding to the curvature of the outer diameter of the arterial wall such that when the first portion 14 is received within the arterial wall, the second portion 22 may be pressed against the outer diameter of the arterial wall. The second portion 22 may further define a flat interior surface and a rounded or bulbous exterior surface such that the second portion 22 protrudes a distance away from the outer diameter of the artery. The distance between the first end 18 and interior surface of the second portion 22 may be prefabricated such that when the second portion 22 is pressed against the arterial wall, the first end 18 is position immediately adjacent to the basement membrane and endothelial cells. Thus, the second portion 22 is configured to operate as a stopper to facilitate the insertion of the first portion 14 to the desired depth within the arterial wall.

Ultrasound may be used to measure the artery wall outer diameter, wall thickness, and inner diameter to determine the appropriate length/size of the housing 12, the first portion 14, and the second portion 22. In particular, the surgeon may select from pre-fabricated bases with a particular height of the first portion 14 and length of the second portion 22 to accommodate differently sized arteries or veins or different wall thicknesses within the same patient or between different patients.

A vital signs sensor module 24 may be releasably or permanently inserted and received within at least a portion of the housing 12. For example, at least a portion of the vital signs sensor module 24 may be inserted through the second open end 20 into the lumen 16 of the housing 12. The module 24 may include a sensor housing 26 that includes one or more biosensors, such as a force or pressure transducer, configured to measure one or more physiological parameters of the patient, which can be transduced and correlated into one or more vital sign measurements. In particular, the sensor module 24 may include a pressure transducer configured to correlate a measured deflection of a diaphragm to a blood pressure waveform and a blood pressure measurement, as discussed in more detail below.

The module 24 may be slideably received within the lumen 16 such that it is retained within the lumen 16 and within the arterial wall. In one configuration, the module 24 includes a capillary tube 28 with an optical fiber 30 or optical sensing mechanism 30, with a transducer diaphragm 32 on its distal tip. For example, the capillary tube 28 may have an optical fiber or optical sensing mechanism 30 disposed within the tube 28 having a rigid, semi-flexible, or flexible diaphragm 32 at its distal end, a portion of which is received within the lumen 16 and positioned to about the tunica intima cells of the artery proximate the first open end 18.

Figure 2:
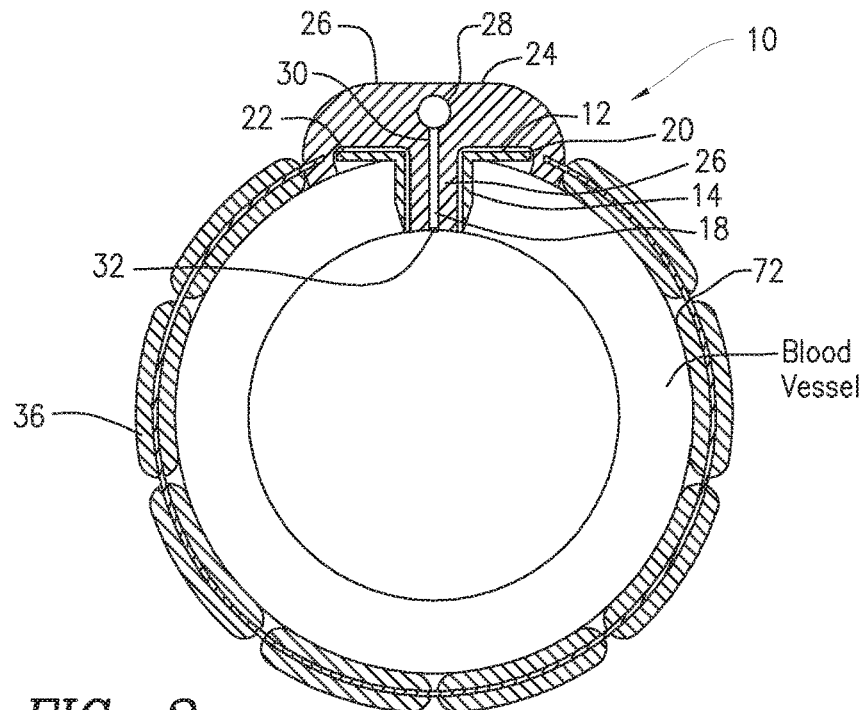
FIG. 2 is a front cross-sectional view of the implantable sensor shown in FIG. 1 implanted within a blood vessel wall.

As shown in FIG. 1-2, the optical fiber 30 extends through the housing 26 and extends outward from the artery in a position substantially perpendicular to the length of the artery, but may extend in any direction. In one embodiment, the optical fiber 30 is not required and an optical sensing mechanism may be included as part of the module 24 to measure the displacement of the diaphragm 32 with each pulse to measure the blood pressure (BP) waveform. Each pulse through the artery or vein may cause the tissue and diaphragm 32 to move inward/outward a distance proportional to the energy of the pulse wave, which may be correlated to produce a measurement of the BP waveform. In one embodiment, the waveform may be calibrated to produce an absolute blood pressure measurement using an external reference blood pressure sensor and an external atmospheric-barometric reference pressure sensor. In an exemplary configuration, the diaphragm 32 may be covered only by the endothelial cells, basement membrane, and/or a small amount of connective tissue. In one configuration, the optics and electronics may be housed within the sensor housing 26 and the capillary tube 28 and the diaphragm 32 may be housed within lumen 16. Once implanted in the body, the basement membrane and endothelial cells may grow from the edges of the injured artery wall tissue, over the surface of the diaphragm 32 to produce a continuous biocompatible/hemocompatible interface. The outer surface of the flexible diaphragm 32 and distal portion of the housing 12 may be textured or coated with compounds that promote healing of the artery wall tissue and the adhesion of the basement membrane and endothelial cell tissue. The very thin layer of cells and/or connective tissue that may cover the outer surface of the diaphragm 32 may stabilize, and not affect, the measurement of the intravascular blood pressure waveform. An external blood pressure reference sensor may be used to compensate for changes in the motion of the diaphragm 32 due to change in the diaphragm 32 material and changes in the layer of cells and connective tissue that may cover the diaphragm 32. Calibrations of the external blood pressure reference sensor may be performed in intervals or as needed to produce an accurate blood pressure measurement.

Examples of pressure transducers that may be included in the sensor module 24 include those with single or multiple deflectable diaphragms 32 with a Wheatstone bridge configuration, a single or multiple piezoelectric crystal configuration, or an optical configuration that accurately measures diaphragm 32 motion. Because the diaphragm 32 is positioned adjacent to the layer of tunica intima, the module 24 may produce an accurate measurement of the intravascular blood pressure waveform without distortion and without compressing or flattening of the artery wall, the artery lumen, the vein wall, or the vein lumen.

After implantation, the outer surface of the diaphragm 32 may remain clean or become coated with protein, carbohydrate, lipid and other compounds. The outer surface of the diaphragm 32 can also become coated with basement membrane, other connective tissue and endothelial cells. The surface of the diaphragm 32 may be textured or coated with a natural or synthetic biomaterial to enhance the adhesion of basement membrane and endothelial cells (tunica intima). Coating the outer surface of the diaphragm 32 with connective tissue or cells may change the physical characteristics of diaphragm 32 motion. This coating layer (not shown) may become stable within days to weeks of implantation in the body. The diaphragm 32 may also have a coating that inhibits the adhesion or attachment of proteins, connective tissue, endothelial cells, platelets, or coagulation factors. The diaphragm 32 may also have a coating of graphene, metal, glass, plastic, or ceramic. Thus, the implanted pressure/force sensor remains stable over time and may require infrequent re-calibration using an external BP cuff measurement system as a reference. The reference BP cuff may also contain a barometer and thermometer (measures atmospheric pressure and temperature) to enhance calibration of the implanted BP sensor.

In other configurations, the transducer's diaphragm 32 may be positioned exterior to the arterial wall, any depth within the arterial wall, or within the artery lumen exposed to flowing blood. For example, a post (not shown) may be located within the flowing blood (artery lumen) with a diaphragm 32 on its distal end or on the side of the post. The intravascular post may be inserted at a right angle to the inner wall of the artery (90 degrees) or any angle relative to the inner wall of the artery (+320 to 0 to −320 degrees). The module's 24 diaphragm 32 may be positioned on the side of the post toward the flow of blood and any position relative to the flow of blood, (0 to 360 degrees). The intravascular post BP sensor module 24 can also be re-calibrated using a reference upper arm BP cuff. An external barometer and thermometer may be used to measure changes in atmospheric pressure and temperature to enhance calibration accuracy of the implanted BP sensor's output signal. In one embodiment, the thermometer may be disposed inside the sensor housing 12 and may monitor a patient's core temperature and the performance of the optical sensor.

The module 24 may further be configured to measure a patient's blood pressure waveform in real-time. The waveform may be analyzed to determine: heart rate, heart rate variability, stroke volume, stroke volume variability, myocardial contractility, vascular resistance, systolic and diastolic timing interval, aortic and mitral valve function, blood flow, and respiratory rate/pattern of ventilation. For example, the sensor modules 24 may include a processor configured to correlate the measured physiological parameters into a vital signs measurement that can be transmitted and/or stored with a memory. The module 24 may further include one or more additional vital signs sensors disposed within the housing 26 or disposed along or within other portions of the module 24. For example, a hemoglobin oxygen saturation sensor, temperature sensor, an ECG electrode, an acoustic sensor such as a microphone, and an activity sensor may be included as part of the module 24, as discussed in more detail below.

The module 24 may include a sensor module retaining element 34 disposed around the circumference of the artery or vein. The sensor module retaining element 34 may be made from an elastic material that may secure the sensor housing 12 and the module 24 within the artery wall tissue while allowing the artery to expand and contract with each pulse. The sensor module retaining element 34 may include a plurality of links 36, each link 36 being movably connected to an adjacent link 36 to define a partial perimeter around the artery or vein. The plurality of links 36 may connect to the sensor housing 26 or the second portion 22 to completely surround the artery or vein. The movability of the links 36 allows for the artery to pulse as blood flows through it without constricting the artery or vein and maintaining contact of the housing 26 with the arterial or venous wall. The mechanism holding the links to each other the sensor module and the blood vessel wall may have a small, moderate, or large degree of elasticity. The inner surface of each link 36 may further define a porous/textured surface such that it may fuse with the arterial or venous wall tissue such that the arterial or venous wall and the links 36 may move substantially simultaneously during pulsatile blood flow. The links may also have one or more through and through openings or channels that permit the ingrowth of vessel wall tissue and vasa vasorum. A hemoglobin oxygen saturation sensor (pulse oximeter-SpO$_2$) 38 may be integrated within the body of one or more links or the housing 26. For example, in a configuration with five links 36 disposed around the circumference of the artery, a component of the SpO$_2$ sensors 38 may be affixed within one or more links 36 to provide for a plurality of photoplethysmograph waveforms and SpO$_2$ measurements. In one configuration, each link 36 has a recess (not shown) sized to receive one of the SpO$_2$ sensor components, for example, the light source and/or detector such that the only barrier between the blood flow within the artery and the SpO$_2$ sensor 38 is the arterial wall tissue. The pulse oximeter light source and light detector may be located on the same link or separate links located on opposite sides of the artery. Each SpO$_2$ sensor 38 may be in communication with the processor inside the housing 28, for example, by a conductor disposed within the sensor module retaining element 34 connecting each SpO$_2$ sensor to each other and to the processor. Optionally, other sensors, for example, an ECG sensor or other electrodes may be disposed within or around the sensor module retaining element 34. For example, electrodes may be disposed on opposite sides of the sensor module retaining element 34 to measure the electrocardiogram, volume of blood flow, rate of blood flow, temperature, heart/lung/upper airway/gastrointestinal sounds, respiratory rate, and pattern of ventilation.

Figure 3B:
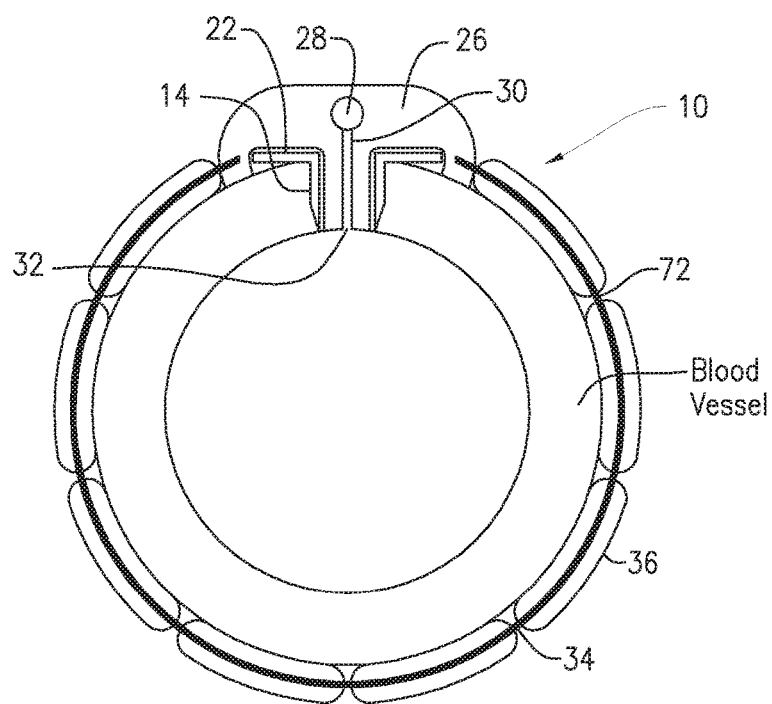
FIG. 3B is a front cross-sectional view of the implantable sensor shown in FIG. 3A.
Figure 4:
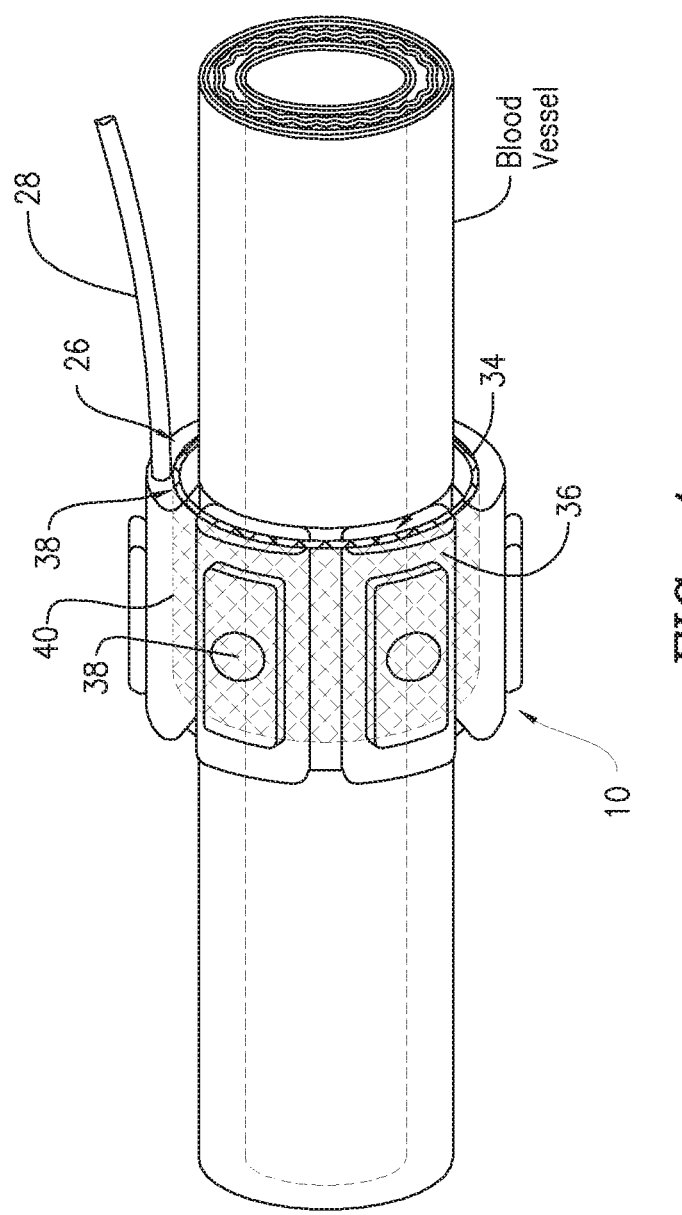
FIG. 4 is a front cross-sectional view of the implantable sensor shown in FIG. 1 with an outer flexible stent or a flexible fabric that holds the sensor against the blood vessel wall and within the blood vessel wall tissue.

Now referring to FIG. 4, in other configurations, the sensor housing 26 may be secured to the outside wall of the artery with a flexible and elastic stent, fabric, or mesh 40 disposed within a portion of the links 36. These materials may have an open structure to decrease mass and facilitate the ingrowth of tunica adventicia and vasa vasorum. For example, the sensor housing 26 may be fabricated with a flexible stent 40 sized to be disposed around the circumference of the artery to affix the capillary tube 28 and transducer diaphragm 32 within the lumen 16. The stent, fabric, or mesh 40 may be non-biodegradable such that it may not degrade overtime, or alternatively, may be biodegradable such that over a predetermined amount of time the stent, fabric, or mesh 40 may degrade leaving the module 24 affixed to the tunica adventicia tissue and the capillary tube 28 affixed to the artery wall tissue. The stent, fabric, or mesh may define a larger diameter to that of the module 24 to surround the module 24 and stents 40. The stent, fabric, or mesh may be made out of natural or synthetic materials that are elastic and flexible, including polymers and biopolymers such as silicone, ePTFE, Dacron®, polyurethane, polypropylene, PHEMA, polylaetate, PLG, collagen, elastic, hyaluronic acid, composites, graphene/carbon nano-tubes, metals and ceramics. Surgical clips, sutures, or a tissue adhesive are further contemplated to be used to secure the module 24 to the artery wall tissue in combination with the stent 40 or as an alternative. For example, as shown in FIG. 3B, sutures are thread through a portion of each link 36 and attach directly to the module 24. Each link 36 may define one or more apertures or channels through with the sutures, belts, or stents 40 may be disposed to facilitate securing the housing 26 to the arterial wall.

Figure 5:
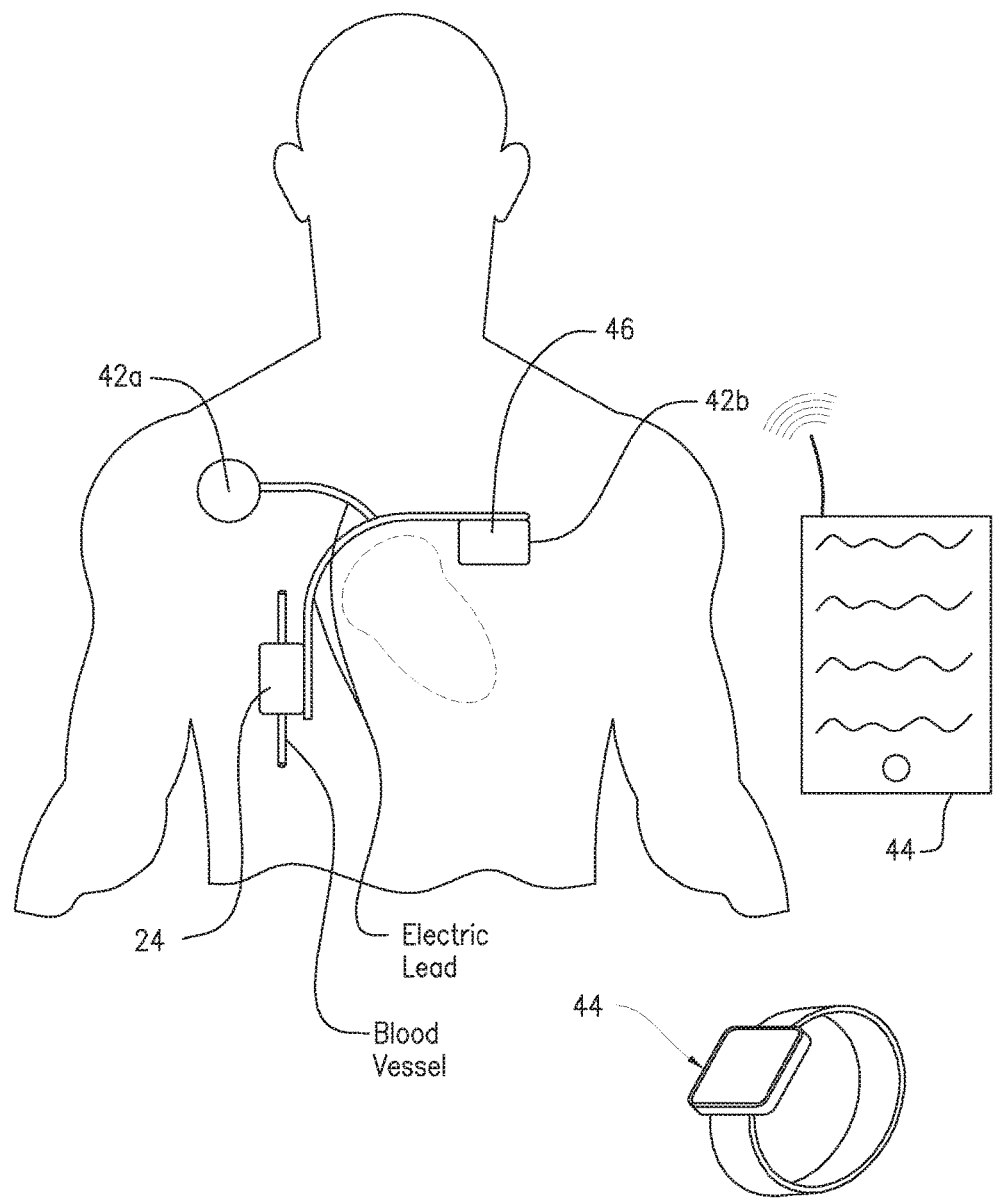
FIG. 5 is a system view of exemplary implanted vital signs sensors in communication with a watch and tablet computer.

Referring now to FIG. 5 which illustrates the location of sensor module 24 implanted around the right internal mammary artery and an additional sensor module 42a implanted within the subcutaneous tissue of the right upper chest wall, and a second additional sensor module 42b implanted within the subcutaneous tissue of the left upper chest wall. Each sensor module 24, 42a, and 42b, can be constructed with one or multiple vital sign sensors per module. For example, subcutaneous tissue sensor modules 42a and 42b may include an EKG electrode, a microphone, a GPS sensor, an accelerometer, and a temperature sensor. The implanted blood pressure sensor 26 may be connected to one or more subcutaneous tissue sensor modules 42a and 42b using a biocompatible lead. One or more of the subcutaneous tissue sensor modules 42a and 42b may have a battery, microprocessor, digital memory, diagnostic/therapeutic control algorithms and telemetry to an external display, data analyzer and data recorder. The implanted sensors 24, 42a, and 42b may communicate with an external controller 44 with a display through radiofrequency telemetry. For example, the controller may be a Smartphone, tablet device, or smart watch, such as an iPhone®, iPad®, Apple Watch® 44 (FIG. 5), or FitBit® or another device that receives information, with an application in communication with a processor having processing circuitry configured to communicate with the implanted sensors 24, 42a, and 42b and record and display the measured information. In another example, the Smartphone, tablet device, smart watch or another device may receive information, analyze the vital sign trend data, produce alerts and alarms, and communicate with a patient, care-giver or other medial professional. In one configuration, the user may wear a smart watch with built-in wireless communication to communicate with the implanted sensors 24, 42a, and 42b, correlate the measured data, and display the results. The controller 44 may be used by the patient and physician to display and processes the real-time and recorded sensor data, calibrate the sensors, and troubleshoot the sensors. The controller 44 may contain a barometer that measures the real-time atmospheric barometric pressure to produce a calibrated and accurate absolute blood pressure measurement. The controller 44 may contain a thermometer that measures the real-time atmospheric temperature to produce a calibrated and accurate absolute blood pressure measurement.

The implanted sensors 24, 42a, and 42b may be in communication with a charge storing device (battery) 46 implanted within the body separate from the sensors 24, 42a, and 42b or within the sensor module 24, 42a, or 42b. The charge storing device 46 may be a hermetically sealed battery implanted within the body in wired communication with the implanted sensors 24, 42a, and 42b. The implantable battery 46 may be re-charged across the skin using an external power source by, for example, inductive charging. In an alternate embodiment, the energy for the implanted sensors 24, 42a, and 42b to function may be transmitted from the outside of the body through the skin and the subcutaneous tissue using electromagnetic coupling or light coupling. Transmission of external power to the internal sensors 24, 42a, and 42b requires low energy and thus a short transmission distance. The external power source may be located near or adhered to the skin surface for extended periods of time to power the implanted vital sign monitoring device or recharge the implanted battery. Internal sensors 24, 42a, and 42b may communicate through radio frequently telemetry and may have an internal power supply or an external power supply.

The module 24 containing the blood pressure sensor may be implanted around the internal thoracic (mammary) artery (between the $3^{rd}$-$4^{th}$, $4^{th}$-$5^{th}$ or $5^{th}$-$6^{th}$ intercostal space) using local or general anesthesia. That artery is located perpendicular to the ribs, approximately 1 cm lateral to the sternum, and between the inner and middle intercostal muscles. In an exemplary configuration, the module 24 may be implanted at the level of the aortic valve to minimize the effects of body position on the arterial pressure waveform and the absolute blood pressure measurement. In an exemplary method of implantation, the surgeon may use a small needle, punch or an automated stapling device to puncture the wall of the artery or vein. In part because the needle may create a tapered opening in the arterial wall, the first portion 14 of the housing 12 may be inserted within the aperture created by the needle such that the first open end 18 is substantially planar or partially recessed from the basement membrane and endothelial cells. In other configurations, the needle may pierce entirely through the wall of the blood vessel. The lumen 16 of the housing 12 may be slid around the circumference of the needle and affixed inside the aperture with the artery wall tissue. The capillary tube 28 of the module 24 may then be inserted within the lumen 16 of the housing 12 for affixation within the housing 12 such that one or more transducer diaphragms 32 may be positioned substantially coplanar with the opening of the first end 18. The elastic element 34 and stents 40 may be positioned around the outside of the artery or vein and attached to the sides of the module 24 to secure the housing 12 within the artery wall tissue and the module 24 to the outside of the blood vessel wall.

Figure 3A:
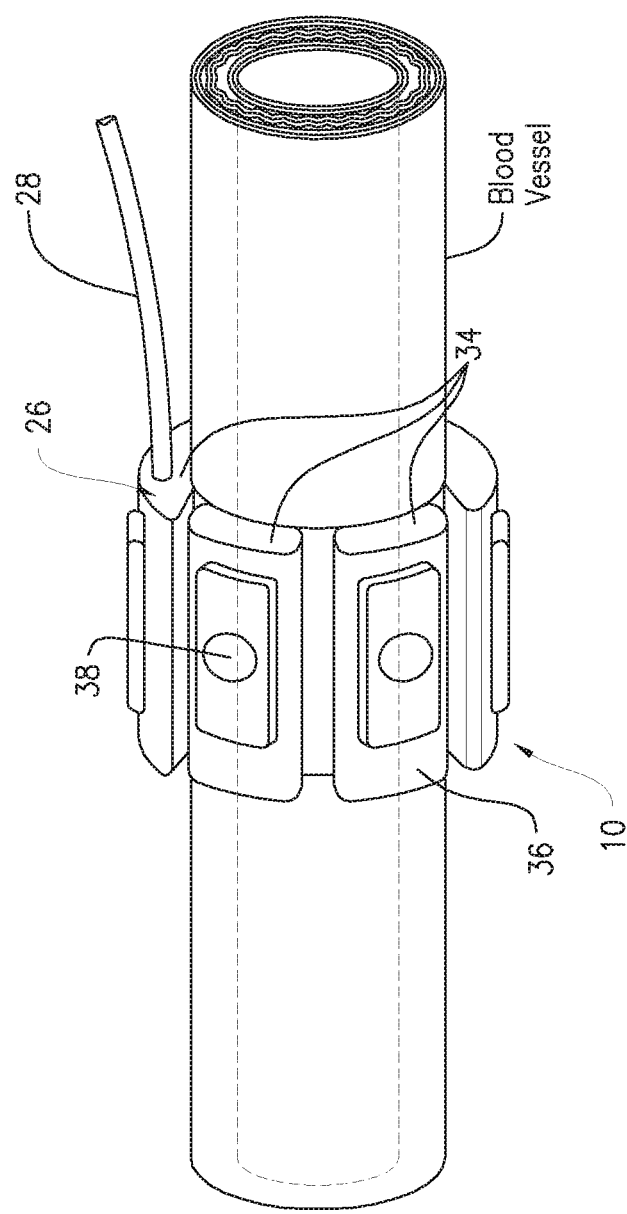
FIG. 3A is a side view of the implantable sensor shown in FIG. 2.

In an exemplary configuration of the module 24, as shown in FIG. 3, two or more blood pressure sensor waveform transducers can be positioned around the artery with the transducer's diaphragm 32 immediately adjacent to the endothelial cells. The $SpO_2$ sensor 38 may be configured with one or more light sources and light detectors external to the artery wall (tunica adventicia); opposite one another (12 o'clock and 6 o'clock positions). This alignment may produce a real-time photoplethysmography signal with a high signal-to-noise ratio and minimal motion artifact. The $SpO_2$ sensor's 38 light sources and detectors may also be located within the artery wall tissue adjacent to the endothelial cells. The external surface of the module 24 (containing the BP sensor and $SpO_2$ sensor), the stents 40, and the additional sensor modules 42a and 42b may have a metal conducting surface, for example, an electrode that can measure the real-time electrocardiogram signal of the heart (ECG or EKG) and electrical signals due to movement of the diaphragm and chest wall. The module 24 and additional sensor modules 42a and 42b may also contain a temperature thermistor that continuously measures the core or blood temperature and one or more microphones that monitor and record the heart sounds (phonocardiogram), lung sounds, upper airway sounds, and gastrointestinal sounds.

The measured vital signs from module 24 and/or implanted sensors 42a and 42b may be used to alert, diagnose, and/or treat associated diseases or conditions that can be correlated from the measured vital signs. For example, measurements taken from one or more of the implanted sensors, namely, ECG, blood pressure waveform, pulse oximeter, thermometer, microphone, accelerometer, GPS may be combined and processed in real-time to provide diagnostic and/or therapeutic recommendations and/or therapies to the patient. Trend data from the implanted sensors can be combined with trend data from one or more non-invasive sensors, for example, a scale measuring body weight, level of activity, body position, sleep patterns, and a camera capturing an image of a patient's head, neck, and torso, and sensors which measure blood pressure and hemoglobin saturation, to provide diagnostic and/or therapeutic recommendations and/or therapies to the patient.

In an exemplary configuration, the one or more measured vital signs may be monitored in an ambulatory patient and displayed and/or stored on the controller 44 or a remote database, for example, to a physician's office and/or a central monitoring station with real-time diagnostic algorithms and a detailed patient electronic medical record (EMR). The measured vital signs may then be compared against a threshold value predetermined by the patient's physician or an algorithm based on the patient's baseline vital sign information. For example, based on the user's weight, height, age, family history, medications, medical history, and prior vital signs data, the algorithm may determine a threshold value or range for one or more of the vital sign measurements that the processor in the controller 44 or a remote location, may compare against each other to determine if a medical condition exists and alert the patient, for example, via a call, text, or alarm to the controller 44, a third-party Smartphone, the patient's Smartphone, or an email that summarizes the condition. The algorithm may trigger an event to record important vital sign sensor data and transmit the trend data to the external control module and central monitoring station for review and clinical analysis. Ambulatory patients may receive audible or visual alerts and alarms when the vital sign sensor algorithms detect a significant change in vital sign trend data. The patient may manually enter a diary of symptoms, signs, meals and medications into the diagnostic/therapeutic software algorithms to manage their disease with greater safety and efficacy. Clinicians at a central monitoring system can communicate with the patient via cell phone to initiate/adjust medical therapy and summarize the effects of that therapy over time. Described below are several diagnostic algorithms that may use multi-modal monitoring (trend data from more than one vital sign sensor) to diagnose the following conditions:

Myocardial Ischemia and Myocardial Infarction—real-time monitoring of the ECG can be used to diagnose myocardial infarction and ischemia by analyzing ST segment depression (horizontal or down-sloping) or elevation in relation to heart rate, BP, & activity level; new onset Q waves; unifocal and multifocal premature ventricular contractions, ventricular tachycardia, ventricular fibrillation; premature atrial contractions; supraventricular tachycardia, atrial fibrillation, new conduction delays, and new heart block related to myocardial ischemia, myocardial infarction and heart failure. Real-time monitoring of the blood pressure waveform can detect changes in BP, heart rate, stroke volume, myocardial contractility, systemic vascular resistance, cardiac output, systolic/diastolic timing intervals, valve function, and respiratory rate that typically occur with myocardial ischemia at rest and with exercise. Real-time monitoring of cardiac sounds can detect wheezing, rhales, S-3 sound, and a new murmur of mitral/aortic valve regurgitation due to myocardial ischemia, LV dysfunction, and pulmonary edema. Real-time monitoring with a pulse oximeter may detect an acute decrease in the arterial hemoglobin oxygen saturation that may occur with myocardial ischemia at rest and with exercise. Changing from a stable to an unstable pattern would be considered a medical emergency requiring increased vigilance and optimized/timely medical therapy.

Congestive Heart Failure and Pulmonary Edema—Real-time monitoring of the blood pressure waveform may be used to detect changes in myocardial contractility, stroke volume, stroke volume variability, heart rate, heart rate variability, systolic/diastolic timing intervals, valve function and respiratory rate that may occur with myocardial ischemia, infarction, cardiomyopathy and heart failure. Real-time monitoring of cardiac & lung sounds can detect wheezing, rhales, S-3 sound, and a new murmurs due to LV dysfunction and acute pulmonary edema. Real-time monitoring with a pulse oximeter may detect an acute decrease in the arterial hemoglobin oxygen saturation. Changing from a stable to an unstable pattern would be considered a medical emergency requiring increased vigilance and optimized/timely medical therapy.

Hypertension (Mild, Moderate & Severe) real-time monitoring of the blood pressure waveform pattern may be used to diagnose hypertension (mean, systolic & diastolic BP>target range for age) and determine the effectiveness of medical/drug/device therapy. For example, a sustained upward trend for systolic, diastolic, and mean blood pressure and/or persistent tachycardia in relation to activity, rest, and sleep may require a change in medication or medial therapy. Medication dose may be adjusted to real-time BP data and trend data. Monitoring the ECG can detect the acute and chronic effects of hypertension on left ventricle wall thickness and myocardial electrical activity (LV hypertrophy with strain pattern). New onset moderate/severe hypertension or changing to an unstable BP pattern would be considered a medical emergency requiring increased vigilance and optimized/timely medical therapy.

Atrial Fibrillation or Supraventricular Tachycardia—real-time monitoring of the ECG can diagnosis new onset or recurrent atrial fibrillation and/or supraventricular tachycardia that occurs spontaneously or secondary to myocardial ischemia, CHF, or hypertension. Real-time monitoring of the arterial BP waveform can detect the hemodynamic significant of an arrhythmia (decreased BP, stroke volume, and cardiac output). Monitoring the pulse oximeter during the arrhythmia can detect decreased hemoglobin oxygen saturation due to decreased and unstable blood flow. New onset atrial fibrillation, SVT or changing to an unstable rhythm pattern would be considered a medical emergency requiring increased vigilance and optimized/timely medical therapy.

Acute Bronchospasm (Asthma)—Changes in the vital signs measurements may be used to diagnose upper airway obstruction, large airway obstruction, small airway obstruction, bronchospasm (due to asthma or bronchitis), and pneumothorax. Real-time monitoring of cardiac, lung, and upper airway sounds can detect wheezing, rhales, rhonchi, increased respiratory rate/tidal volume (minute ventilation) and prolonged exhalation (increased work of breathing). Monitoring the arterial BP waveform can detect increased heart rate, increased heart rate variability, decreased stroke volume, increased stroke volume variability, and decreased cardiac output. Monitoring the ECG can detect an increased HR, decreased HR variability, arrhythmias, and acute right ventricle strain. Monitoring the pulse oximeter can detect an acute decrease in hemoglobin oxygen saturation. New onset bronchospasm with a high work of breathing and decreased hemoglobin oxygen saturation would be considered a medical emergency requiring increased vigilance and optimized/timely medical therapy.

Chronic Obstructive Pulmonary Disease & Respiratory Failure—Changes in the vital signs measurements may be used to diagnose acute respiratory failure and a worsening of chronic bronchitis and emphysema due to acute bronchitis or pneumonia. For example, an increase in respiratory rate and minute ventilation, coughing, wheezing, decreased hemoglobin oxygen saturation, persistent tachycardia, myocardial ischemia, right heart strain, and elevated temperature may be indicative of such a condition. A persistently high work of breathing and decreased hemoglobin oxygen saturation would be considered a medical emergency requiring increased vigilance and optimized/timely medical therapy.

Intestinal Diseases (Crohn's Disease, Ulcerative Colitis, Diverticulitis, Ischemia)—Changes in the vital signs measurements may be used to diagnose decompensation of inflammatory bowel disease. For example, increased/decreased bowel sounds (motility), elevated temperature, tachycardia, hypotension, decreased blood flow, tachypnea, decreased hemoglobin oxygen saturation may all be indicated of such a condition.

Pulmonary Embolism—Changes in the vital signs measurements may be used to diagnose a pulmonary embolism. For example, acute onset wheezing, increased respiratory rate, increased minute ventilation, tachycardia, atrial/ventricular arrhythmias, right ventricle strain pattern on EKG, decreased hemoglobin oxygen saturation, elevated temperature, decreased stroke volume, decreased cardiac output, and hypotension, may be indicated of such a condition. Any pulmonary embolism would be considered a medical emergency requiring increased vigilance and optimized/timely medical therapy.

Hemorrhage or Dehydration—Changes in the vital signs measurements may be used to diagnose significant dehydration due to bleeding, edema, decreased oral intake, excess urination, or diarrhea. For example, increase in heart rate, peripheral vascular resistance, respiratory rate, minute ventilation and a decrease in stroke volume, cardiac output, blood pressure, blood flow, and hemoglobin oxygen saturation, may be indicated of moderate to severe blood loss and/or dehydration.

The above conditions are merely exemplary of the number of ways the vital sign measurements determined from the sensor module 24 and/or additional sensor modules 42a and 42b may be measured and correlated in real-time against a patient established threshold to either signal an alert to the user, signal an alert to a medical professional (primary care physician or central monitoring station), or record the data or additional data for further evaluation. For example, a patient with known atrial fibrillation may have a different blood pressure threshold value compared to the blood pressure of a patient without atrial fibrillation. As such, the threshold value can be programmed by the doctor into the controller 44 or automatically by the remote database, such that when that threshold value is exceeded or falls below that threshold in a real-time ambulatory setting, depending on the threshold value, an alert may be sent to the patient, the central monitoring station, and/or the patient's physician. Similarly, patients with other conditions may have different thresholds for each vital sign measurement measured by the module 24 and/or 42 and 42b such that each module 24 in combination with the controller 44 may be personalized for each patient to provide an early warning sign of an individual condition prior to an adverse event. Alerts and alarms can be based upon a simple threshold, a predicted threshold, or based upon a model of the patient's physiology. Moreover, based on the vital signs measurements, a therapeutic algorithm may also be used in combination with the diagnostic algorithm to recommend and/or implement therapies for the patient based on the measured vital signs compared to the patient's individual threshold values or ranges. For example, the therapeutic algorithm may operate in the above conditions as follows:

Myocardial Ischemia—Physicians and patients currently titrate medications in response to symptoms such as "chest pain" (angina) despite the fact that greater than 80% of myocardial ischemia is silent and many "pains in the chest" are due to non-cardiac causes. Medications for ischemic heart disease may be dosed once or multiple times per day based upon quantitative vital sign data. Real-time data may be used to "recommend" an adjustment in medical therapy (nitrates, ACE inhibitors, beta blockers, calcium channel blockers, aspirin, anticoagulant, and oxygen) based on the patient's medical history and historical vital signs measurements. It is further contemplated that the real-time vital sign sensor system and closed-loop therapeutic algorithms may automatically deliver anti-ischemia medications using drug infusion pumps and/or oxygen using an oxygen source and regulator. Real-time data may also be used to automatically adjust electrical nerve tissue stimulation devices and cardiovascular blood pump devices that optimize blood pressure and blood flow in a patient with a sick heart.

Congestive Heart Failure & Pulmonary Edema—Changes in the patient's vital sign pattern may be used to detect the onset of CHF and pulmonary edema in the early stages as discussed above, such that management can occur in the ambulatory setting; avoiding a visit to the emergency room and admission to an intensive care unit. Real-time vital sign sensor data may be used to recommend an acute change in medical therapy (diuretics, catechamines, digitalis, nitrates, beta blockers, calcium channel blockers, ACE inhibitors, and oxygen). It is further contemplated that the real-time vital sign sensor system and closed-loop therapeutic algorithms may automatically deliver medications, oxygen, pacemaker therapy, ventricular assist device therapy, and total artificial heart therapy that may increase myocardial contractility, control HR, control BP, control blood flow, oxygen concentration, and decrease systemic vascular resistance using drug infusion pumps and electrical stimulation.

Hypertension—Real-time analysis of the BP waveform may calculate heart rate, heart rhythm, stroke volume, arterial blood flow, myocardial contractility, and systemic vascular resistance. Vital sign sensor data may be used to recommend an acute change in medical therapy (diuretics, beta blockers, alpha blockers, vasodilators, ACE inhibitors, calcium channel blockers) and monitor the effectiveness of that medical therapy. It is further contemplated that the real-time vital sign sensor system and closed-loop therapeutic algorithms may automatically deliver anti-hypertension medications using drug infusion pumps and electrical therapy of nervous tissue to maintain the mean, systolic, and diastolic BP is the target range during rest, exercise, sleep, and illness.

Arrhythmia—real-time vital sign sensor data may be used to recommend an acute change in medical therapy (beta blockers, calcium channel blockers, and membrane stabilizers). It is further contemplated that real-time vital sign sensor system and closed-loop therapeutic algorithms may automatically deliver anti-arrhythmia medications using drug infusion pumps; and anti-arrhythmia electrical shock therapy using a defibrillation shock, a cardioversion shock and/or override pacemaker shocks.

Asthma—real-time vital sign sensor data may be used to recommend medical therapy (oxygen, catecholamine inhaler, steroid inhaler, parenteral catecholamines) during an acute asthma attack. It is further contemplated that the real-time vital sign sensor system and closed-loop therapeutic algorithms may automatically deliver anti-inflammatory and bronchodilator medications using drug infusion pumps, oxygen using an oxygen source/regulator, and electrical stimulation of nervous tissue to reduce bronchospasm and inflammation.

Chronic Obstructive Pulmonary Disease (COPD)—real-time vital sign sensor data may be used to recommend an acute change in medical therapy (oxygen, catecholamine inhaler, steroid inhaler, parenteral catecholamines). It is further contemplated that the real-time vital sign sensor system and closed-loop therapeutic algorithms may automatically deliver anti-inflammatory and bronchodilator medications using drug infusion pumps, oxygen using an oxygen source/regulator, and electrical stimulation of nervous tissue to reduce bronchospasm and inflammation.

Chronic Intestinal Diseases—real-time vital sign sensor data may be used to recommend an acute change in medical therapy (intravenous fluids, oxygen, enteral/parenteral steroids, and enteral/parenteral anti-inflammatory medications). It is further contemplated that the real-time vital sign sensor system and closed-loop therapeutic algorithms may automatically deliver anti-inflammatory, pro-peristalsis, or anti-peristalsis medications using drug infusion pumps.

The measured vital signs data may further be processed to determine whether trend vital sign data is "abnormal" or "extreme" relative to a model of a universal healthy/stable patient or adapted to an individual patient. For example, hundreds to thousands of hours of patient vital sign data from any one or all of the sensors may be recorded and analyzed. Large data sets may be split into (1) training sets, (2) control sets, and (3) test sets. Clinical experts may review the trend data and label specific patterns as "crisis events" or "error codes." The algorithms may learn from an individual patient's physiological patterns and determine when the trend data is "abnormal" or "extreme" with high sensitivity and specificity (minimal false alerts/alarms and few missed "real" events). The real-time method may estimate the extreme value distributions of multivariate, multimodal mixture models for analysis of complex datasets from an array of physiological vital sign sensors.

Figure 6:
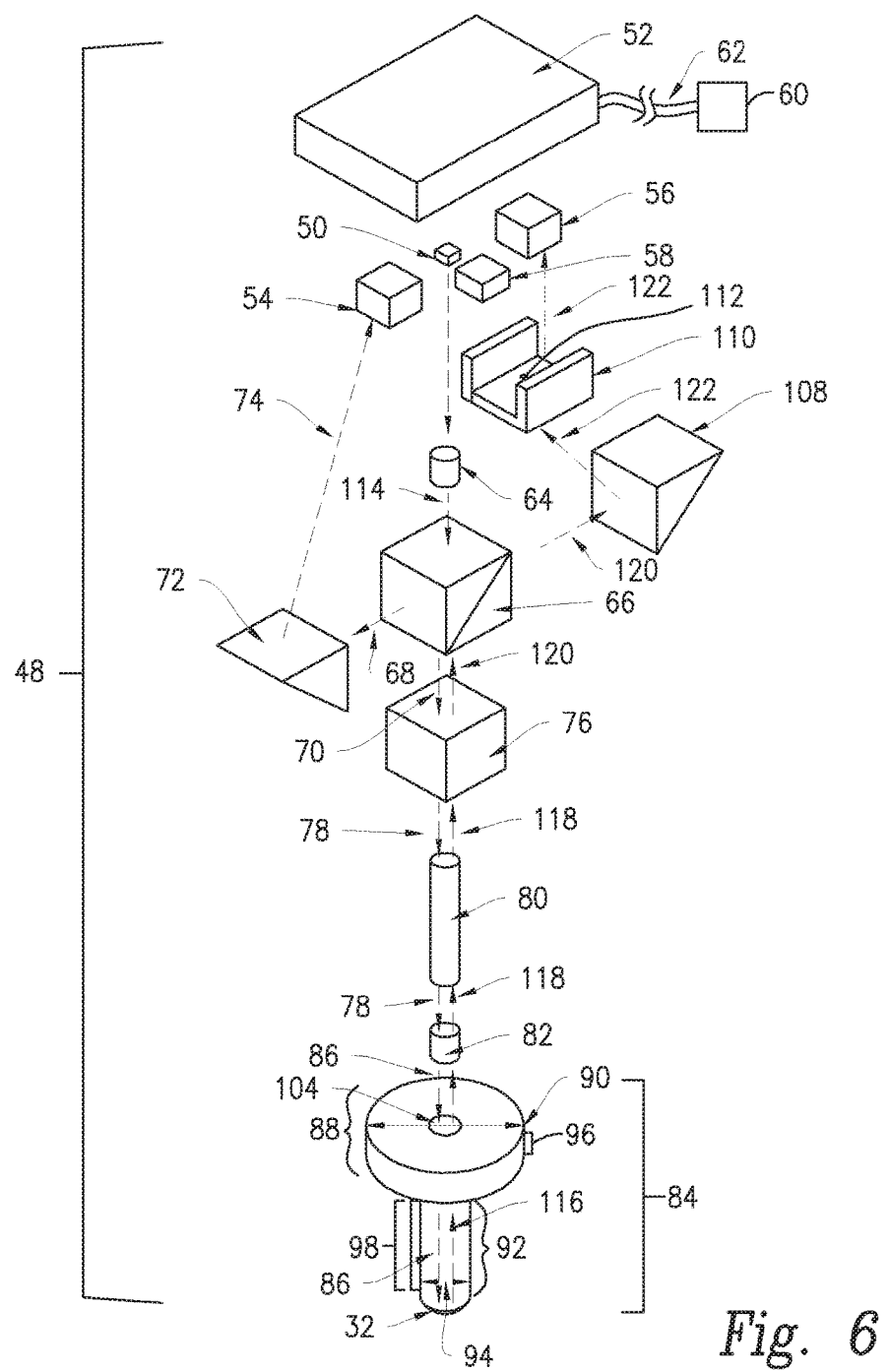
FIG. 6 is an exploded view of an embodiment of a confocal displacement sensor.

Referring now to FIG. 6, the implantable vital signs sensor device and monitoring system 10 may include a confocal displacement sensor 48. The sensor 48 may include different optical components that cooperate and form the sensor 48. Epoxy adhesives, other types of glues, optical contact bonding, or other types of bonding methods may be used to secure the optical components together. The bonding or securing of the optical components of the sensor 48 may make a monolithic integrated circuit or an integrated circuit. This may reduce sensor 48 shock and vibration and may make it less susceptible to alignment creeps. The sensor 48 may be sized to fit within the wall of a blood vessel and/or may be sized to be at least partially inserted within the wall of the blood vessel.

The sensor 48 may include a light source 50 configured to emit light which may span the optical spectrum from ultraviolet to infrared wavelengths. The light source 50 may be a laser, such as a vertical cavity surface emitting laser (VCSEL) configured to emit coherent light, or it may be a light source such as a lens emitting diode (LED) configured to emit incoherent light. In an exemplary embodiment, the light source 50 may be a VCSEL with a wavelength of 850 nm. In the configuration as shown in FIG. 6, the light source 50 may be a single light source, however, any number of light sources may be included. In a configuration where multiple light sources 50 are used, the light sources 50 may be multiple lasers emitting at multiple discreet wavelengths or may be multiple LEDs emitting to cover a continuous broadband spectrum.

The light source 50 may be in communication with a drive circuitry 52 which may include electronic traces and bond pads to operate the light source 50, a reference detector 54, a signal detector 56, and a temperature sensor 58. In addition, the drive circuitry 52 may include electronic components such as trans-impedance amplifiers (TIA), resistors, capacitors, etc. needed to optimize performance of the sensor 48. In one embodiment, the drive circuitry 52 may be connected with a biocompatible flexible lead to processing circuitry 60. The processing circuitry 60 may be disposed proximate the drive circuitry 52 or it may be located within the sensor 48 or external to the sensor 48. In addition to a traditional processor and memory, the processing circuitry 60 may comprise integrated circuitry for processing and/or control, e.g., one or more processors and/or processor cores and/or FPGAs (Field Programmable Gate Array) and/or ASICs (Application Specific Integrated Circuitry). The processor may be configured to access (e.g., write to and/or reading from) memory, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory). Such memory may be configured to store code executable by a processor and/or other data, e.g., data pertaining to communication, e.g., configuration and/or address data of devices, etc. Processing circuitry 60 may be configured to control any of the methods which may include correlating a measured intensity of light into a measurement of blood pressure and/or to cause such methods and/or processes to be performed, e.g., by the sensor 48. The processing circuitry 60 may be in communication with the charge storing device (battery) described above with respect to FIG. 5 which may be configured to provide power to the light source 50. In one embodiment, the processing circuitry 60 may be connected with a flexible lead to different optical components in the sensor 48. In another embodiment, the sensor 48 may have more than one processing circuitries 60 disposed external to the sensor 48.

The sensor 48 may also include the reference detector 54 in communication with the drive circuitry 52. The reference detector 54 may be configured to detect light emitted by the light source and may measure the intensity of the light. The reference detector 54 may include an array of pixel detectors (not shown) configured to detect at least one property of light, for example, the size of the light beam, the spectrum of the light beam, or light intensity. A variety of different reference detector 54 sensitivities may be used in the sensor 48. In other embodiments, there may be more than one reference detector 54 in the sensor 48. Optionally, the sensor 48 may further include a temperature sensor 58 configured to measure the temperature of the drive circuitry 52. With certain calibrations of the temperature sensor 58, the temperature of the body may also be derived based upon the temperature of the drive circuitry 52. Changes in body temperature may be detected by the temperature sensor 58 and may allow a recalibration to occur. The temperature sensor 58 may be disposed proximate to the light source 50 and may be in communication with the drive circuitry 52 through a flexible lead 62.

The sensor 48 may include a first lens 64 configured to collimate the light emitted from the light source 50. The first lens 64 may be disposed proximate to the light source 50 and may be spherical, aspherical or cylindrical in shape. The first lens 64 may be diffractive and Fresnal or it may be electrically controlled including liquid crystal or liquid filled. In one configuration, the first lens 64 may be a gradient-index (GRIN) lens with an outer diameter range of 100-2000 microns, although the first lens 64 may also be any other type of lens as well as a curved mirror. The first lens 64 may be made out of a variety of different materials including glass, plastic, germanium, zinc selenide or sodium chloride. The first lens 64 may be coated with an optical coating including an anti-reflection coating. Different techniques may be used to make the first lens 64 including neutron irradiation, chemical vapor deposition, partial polymerization, ion exchange, ion stuffing and direct laser writing.

The sensor 48 may also include a beam splitter 66 configured to split the light emitted from the light source 50 into a first beam of light 68 and a second beam of light 70. The beam splitter 66 may be disposed distal to the distal end of the first lens 64 and may be in the shape of a cube, a plate, or a prism. The beam splitter 66 may be a polarizing beam splitter and it may have a variety of different optical properties such as polarization sensitivity. In one embodiment, the beam splitter 66 may be polarized and split light emitted from the light source 50 into the first beam of light 68 with one linear polarization and the second beam of light 70 with another orthogonal linear polarization. In the embodiment as shown in FIG. 6, the beam splitter 66 may be in the shape of a cube and may be 1 mm per side.

Disposed on one side of the beam splitter 66 may be a first prism 72 configured to refract light. The first prism 72 may be made of one or multiple mirrors. In one configuration, the first prism 72 may be a three-dimensional right angle triangle, however, the first prism 72 may also be a three-dimensional square or other three-dimensional shape or an electronically controlled microelectromechanical (MEMs) mirror. In one configuration, the first prism 72 may receive the first beam of light 68 from the beam splitter 66 and refract the first beam of light 68 to create a refracted first beam of light 74. The refracted first beam of light 74 may be directed by the first prism 72 toward the reference detector 54 and the reference detector 54 may receive the refracted first beam of light 74. The drive circuity 52 may process the signal received from the reference detector 54 into a reference light measurement.

Disposed distal to the beam splitter 66 may be a wave plate 76 configured to modify the polarization state of light travelling through it. In one configuration, if the beam splitter 66 polarizes light, the sensor 48 may not have a wave plate 76. Birefringent materials including quartz or mica may be used to make the wave plate 76 and the wave plate 76 may be a quarter wave plate or a half wave plate. The beam splitter 66 and the wave plate 76 may be used to create an optical isolator. The wave plate 76 may convert linearly polarized light into circularly polarized light and/or it may convert circularly polarized light into linearly polarized light. The polarization direction of linearly polarized light may be further shifted by the wave plate 76. In an exemplary configuration, the second beam of light 70 with linear polarization may pass through the wave plate 76 where it is polarized into a circularly polarized second beam of light 78.

Figure 7:
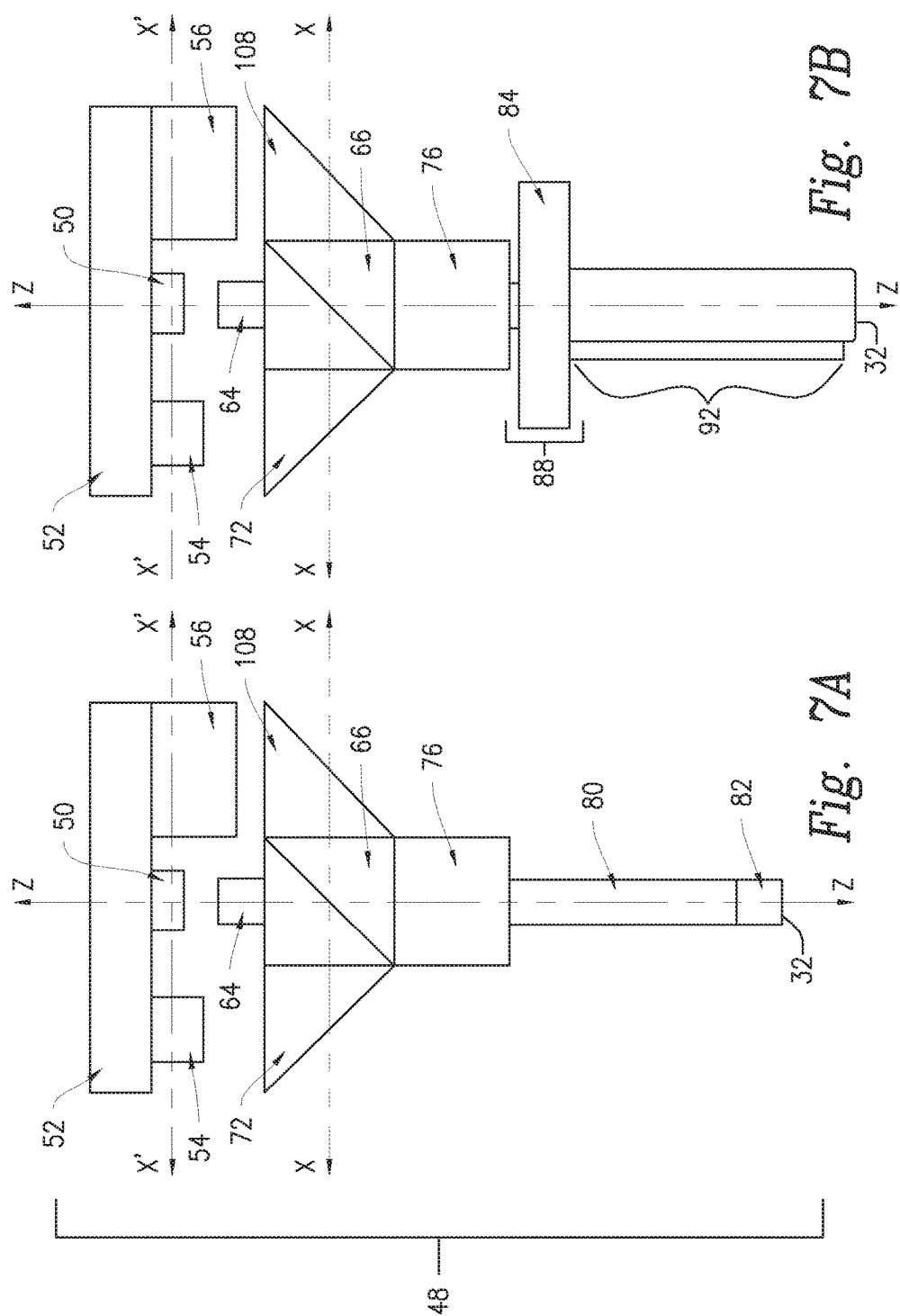
FIG. 7A is a front cross-sectional view of the confocal displacement sensor shown in FIG. 6 without a diaphragm housing constructed in accordance with the principles of the present invention showing three longitudinal axes.
FIG. 7B is a front cross-sectional view of the confocal displacement sensor shown in FIG. 6 with the diaphragm housing.

Referring to FIGS. 7A and 7B, disposed distal to the wave plate 76 may be a spacer 80 configured to space the circularly polarized second beam of light 78 a predetermined distance away from a second lens 82 disposed distal to the distal end of the spacer 80. The spacer 80 may be different shapes and sizes, including a cylinder shape which is hollow as well as a solid rod, depending upon the organization of the optical components within the sensor 48. In one configuration, there may be one spacer 80 or multiple spacers 80 and the one or multiple spacers may be disposed within a diaphragm housing 84. The second lens 82 may be configured to have the same or similar qualities and properties as the first lens 64 discussed in more detail above. The second lens 82 may be configured to converge light. In an exemplary configuration, the second lens 82 may focus the circularly polarized second beam of light 78 creating a further focused circularly polarized second beam of light 86. The further focused circularly polarized second beam of light 86 may then pass through the spacer 80.

Continuing to refer to FIG. 6, the sensor 48 may include the diaphragm 32, as discussed in more detail above with respect to FIGS. 1-5, and the diaphragm housing 84. The diaphragm 32 and the diaphragm housing 84 may be disposed on the distal end of the sensor 48. The diaphragm 32 may be disposed on the distal end of the diaphragm housing 84 and may be configured to reflect light. The diaphragm housing 84 may be configured to receive light and direct it toward the diaphragm 32. The size and shape of the spacer 80 may create a predetermined distance between the light source 50 and the diaphragm 32.

In one configuration, the diaphragm housing 84 may have a first portion 88 which has a first diameter 90 and a second portion 92 which has a second diameter 94. The first diameter 90 of the first portion 88 may be larger than the second diameter 94 of the second portion 92. The first portion 88 of the diaphragm housing 84 may have a first length 96 and the second portion 92 of the diaphragm housing 84 may have a second length 98. The second length 98 may be longer than the first length 96.

Figure 11:
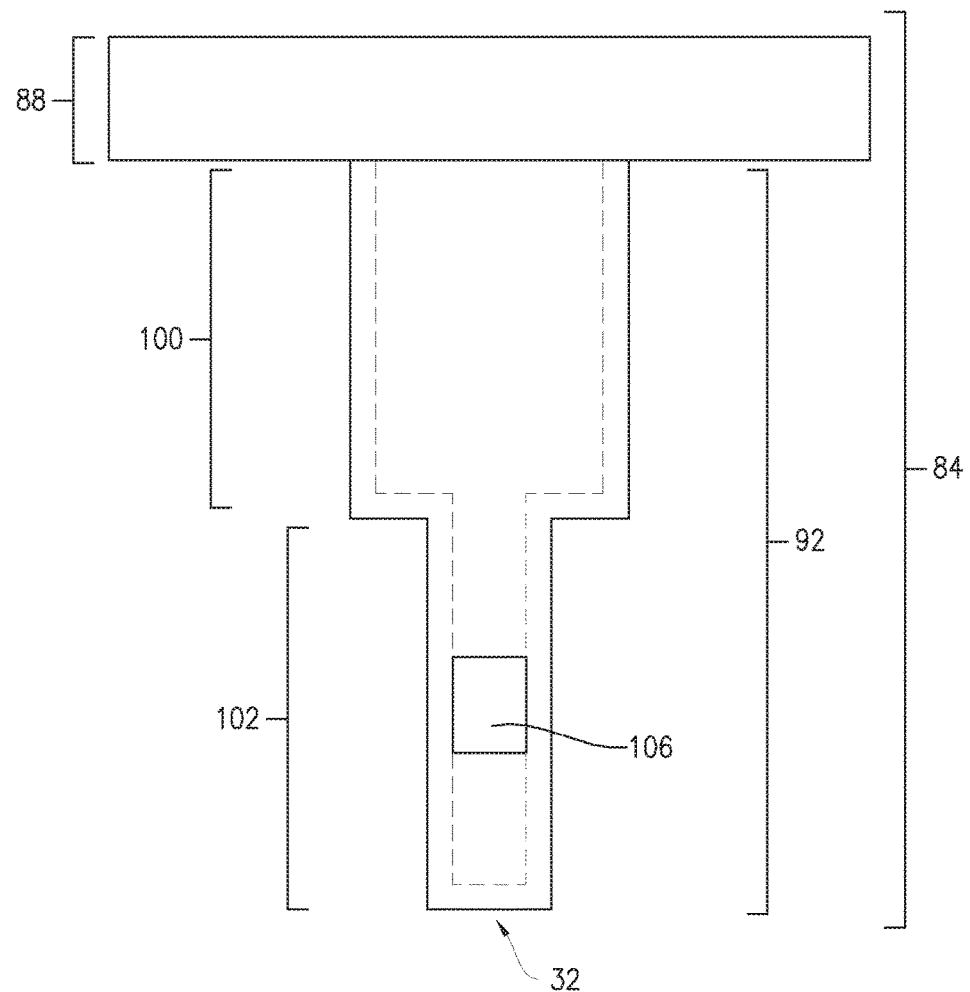
FIG. 11 is a front cross-sectional view of an alternative diaphragm housing of the confocal displacement sensor.

Now referring to FIG. 11, one configuration of the diaphragm housing is shown where the diaphragm housing 84 may have a second portion 92 which has a first segment 100 and a second segment 102. The first diameter 96 of the first portion 88 may be larger than the second diameter of the first segment 100 and the second segment 102. The diameter of the first segment 100 may be larger than the diameter of the second segment 102 and the first segment 100 of the diaphragm housing 84 may be longer than the second segment 102. The length of the first portion 88 may be in a range of 0% to 50% of the size of the outer diameter of the blood vessel and the outer diameter of the first portion 88 may be in a range of 0% to 50% of the size of the outer diameter of the blood vessel. The first segment 100 of the diaphragm housing 84 may have a length in the range of 0%-35% of the size of the outer diameter of the blood vessel, the outer diameter of the first segment 100 may be in a range of 0%-35% of the size of the outer diameter of the blood vessel, and the inner diameter of the first segment 100 may be in a range of 5%-35% of the size of the outer diameter of the blood vessel. The second segment 102 of the diaphragm housing 84 may have a length in the range of 0%-35% of the size of the outer diameter of the blood vessel, the outer diameter of the second segment 102 may be in a range of 0%-35% of the size of the outer diameter of the blood vessel, and the inner diameter of the second segment 102 may be in a range of 5%-35% of the size of the outer diameter of the blood vessel.

The diaphragm housing 84 may also have a lumen 104 through the first portion 88 and the second portion 92. The lumen 104 may be sized to retain the spacer 80 and the second lens 82. In one configuration, the lumen 104 in the diaphragm housing 84 may surround the spacer 80 and the second lens 82. In another configuration, the first segment 100 of the diaphragm housing 84 may secure the second lens 82 and the second segment 102 of the diaphragm housing 84 may space the diaphragm 32 a predetermined distance away from the second lens 82. In another configuration, the lumen in the second segment 102 may have a second spacer 106 disposed between the second lens 82 and the diaphragm 32. The second spacer 106 may be made out of air, gas, or liquid and may have a refractive index to set the focal point of the further focused circularly polarized second beam of light 86 to a predetermined location. Other optical components from the sensor 48 may also be sized to fit inside the lumen 104. In one embodiment of the sensor 48, the diaphragm 32 may be at the distal end of the second portion 92 of the diaphragm housing 84 and may seal the lumen 104 of the diaphragm housing 84 so that blood, water and water vapor may be prevented from entering into the sensor 48 from the blood vessel as may be seen in FIGS. 8 and 9. The diaphragm housing 84 may be made out of different materials including silicone. The silicone may have a variety of compositions which determine the flexibility of the silicone.

Referring to FIGS. 7A and 7B, in one configuration, the diaphragm 32 and the diaphragm housing 84 may be molded together as a unitary piece. In another configuration, the diaphragm 32 and the diaphragm housing 84 may be separate pieces that may be releasably secured or permanently secured together. The diaphragm 32 may be composed of materials including metal, plastic, graphene, and silicone, polymer, glass and ceramic or other elastic materials that are an implantable grade and biocompatible.

Figure 10:
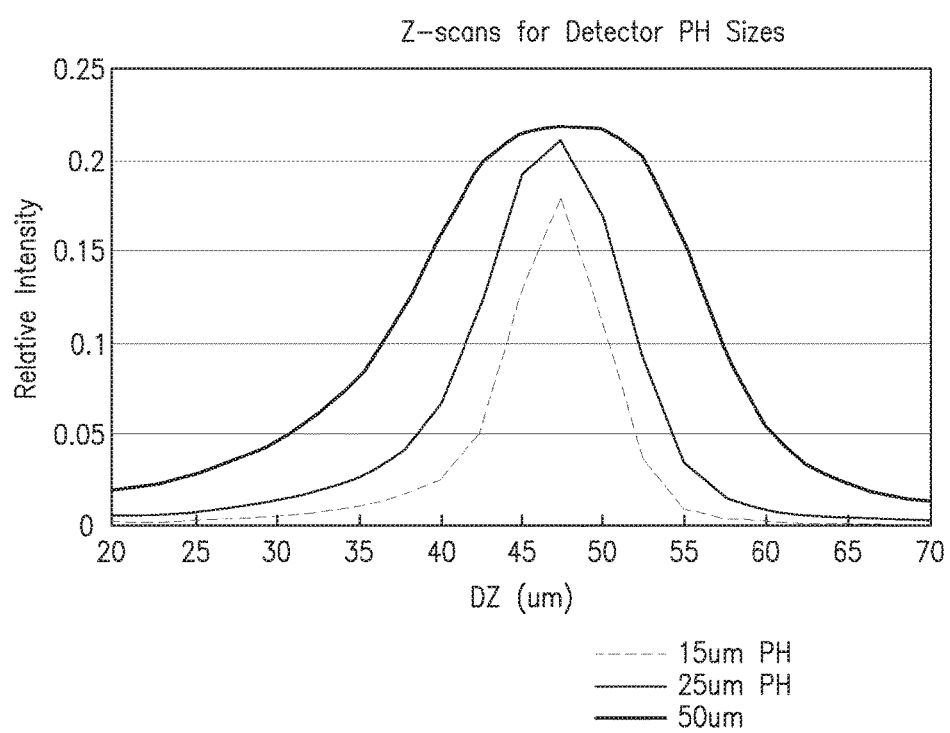
FIG. 10 is an exemplary graph showing how the deflection of a diaphragm in micrometers may correlate with the measured intensity of light.

As discussed above with respect to FIGS. 1-2, the diaphragm 32 may be configured to be deflectable in response to blood pressure changes within the blood vessel and may be elastic and robust so that it may deflect over many different pressure cycles for an extended period of time. For example, the diaphragm 32 may deflect in response to blood pressure in a range between approximately 0 mmHg to at least 250 mmHg. For example, as shown in FIG. 10, the sensor 48 may measure the deflection of the diaphragm 32 and correlate the measured deflection to a blood pressure waveform. The amount of deflection of the diaphragm 32 may correlate to a change in light properties as measured by the sensor 48. When there is a larger deflection of the diaphragm 32, the intensity of the light which is detected by the signal detector 56 may be greater than when there is a smaller deflection of the diaphragm 32.

Figure 8:
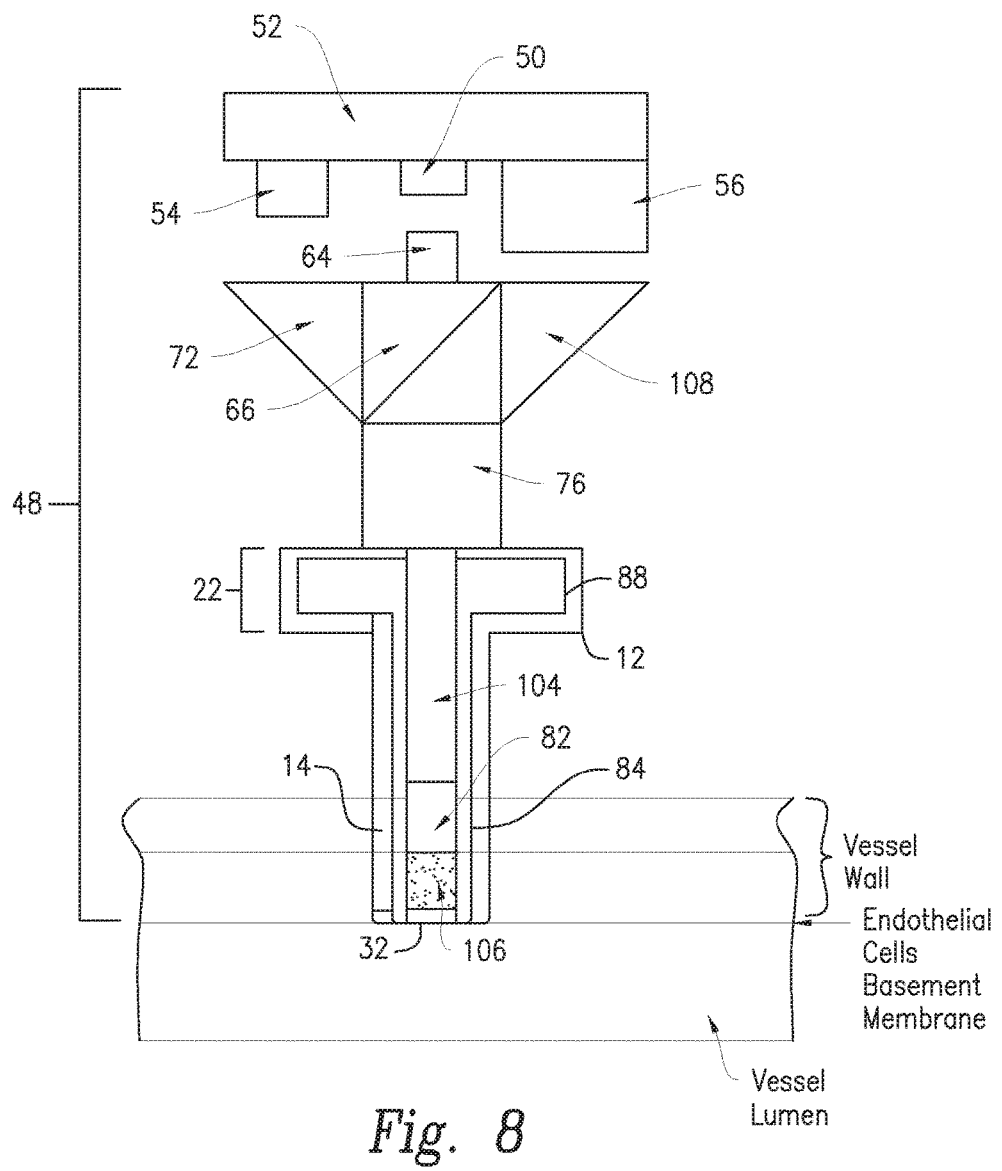
FIG. 8 is a front cross-sectional view of the confocal displacement sensor with a portion of the sensor inserted within the wall of a blood vessel.
Figure 9:
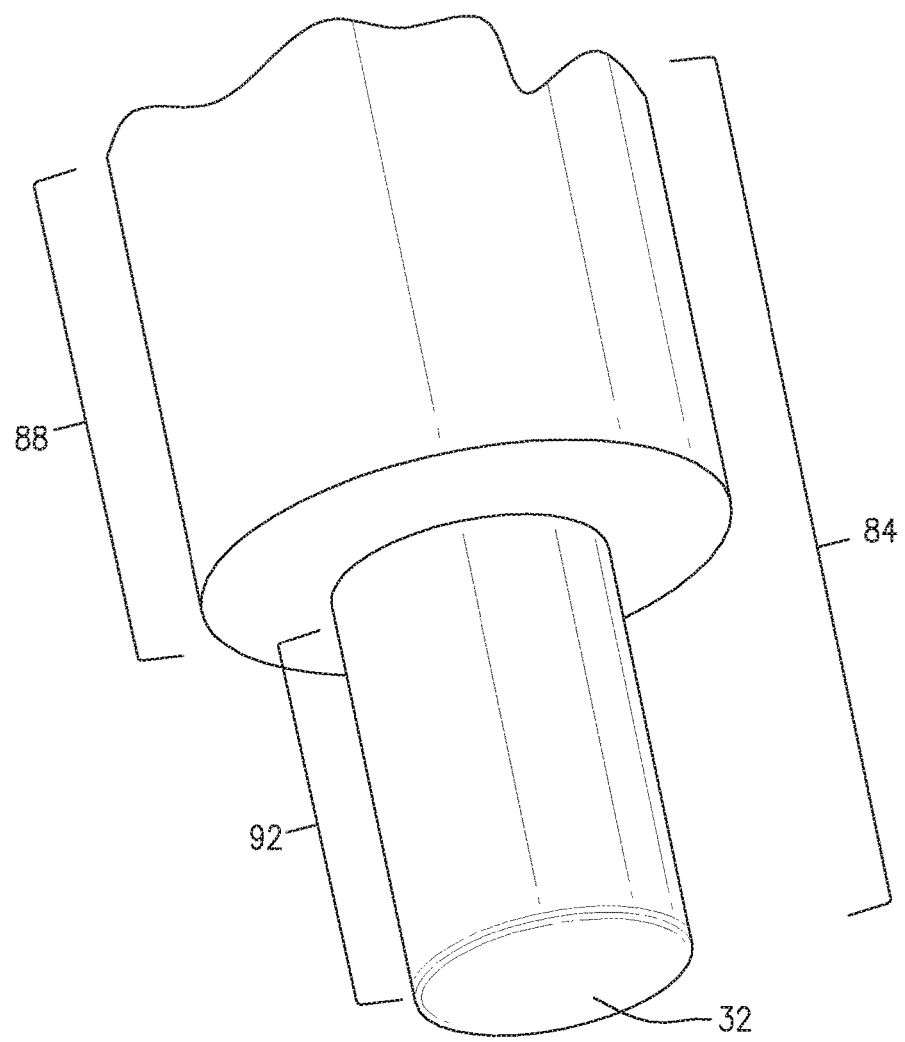
FIG. 9 is a close-up view of the diaphragm and a portion of the diaphragm housing.

Referring now to FIG. 8, the diaphragm 32, the diaphragm housing 84, the second lens 82, and a second spacer 106 may be sized to be at least partially inserted or disposed within the wall of a blood vessel or completely inserted within the blood vessel. In one embodiment, diaphragm housing 84 may be inserted into the lumen 16 of the housing 12. The distal end of the housing 12 and the diaphragm housing 84 may be in contact with the basement membrane as well as the endothelial cells. In one configuration, the housing 12 may be made from solid, rigid and non-deformable materials which isolate lateral forces from body movement that may distort the blood pressure waveform measurement in the sensor 48. In an alternative embodiment, the diaphragm housing 84 may be rigid so it can be inserted directly into a blood vessel. The second portion 92 of the diaphragm housing 84 may be sized to span at least a portion of the blood vessel wall and may be in contact with the basement cells and/or endothelial cells of the blood vessel which grow back after an incision is made to cover at least the diaphragm 32.

Referring back now to FIG. 6, the sensor 48 may include a second prism 108 disposed on the opposite side of the beam splitter 66 as the first prism 72. The second prism 108 may be configured to refract light reflected from the diaphragm 32. The second prism 108 may have the same or similar qualities and characteristics as the first prism 72 as discussed in more detail above.

In communication with the drive circuity 52 may be a gate 110 and a signal detector 56, wherein the gate 110 may be configured to allow a portion of light to pass through it and the signal detector 56 may be configured to receive the light and detect the intensity of the light. The gate 110 may be disposed proximate the signal detector 56 as well as proximate the first prism 108. In one configuration, the gate 110 may be disposed between the second prism 108 and the signal detector 56. In other exemplary configurations, the gate 110 may be disposed in other positions within the sensor 48 and the sensor 48 may have more than one gate 110.

The gate 110 may be different sizes and shapes depending upon the configuration of the optical components within the sensor 48. The gate 110 may contain an aperture 112 and the aperture 112 may be a round pin-hole shape or a long and narrow shape. The aperture 112, depending upon its size, may be configured to only allow a portion of the light to pass through it. In one embodiment, the signal detector 56 may be a Si photodiode with a diameter in the range of 0.1-1.0 mm. The signal detector 56 and the reference detector 54 may include one or more detectors. Each signal detector 56 and reference detector 54 may be configured to measure different properties of light including light intensity, the area of lighting hitting the detector, and wavelength of the light. In one embodiment, the reference detector 54 may be connected to different components of the sensor 48 with a capillary tube or another type of fiber optics.

In an exemplary configuration, the drive circuitry 52 may be a mounting base for the signal detector 56 and/or other optical components in the sensor 48 that require electrical connectivity. The processing circuitry 60 may include circuitry for the amplification of signals received from the reference detector 54 and the signal detector 56. The processing circuitry 60 may be rigid, flexible, partially rigid or partially flexible and made out of materials including FR4, ceramics and biocompatible materials. The drive circuitry 52 may also have an interface connector, the interface connector may connect to a source which may include a flexible lead.

Referring now to FIGS. 7A and 7B, in one configuration, the light source 50, the first lens 64, the beam splitter 66, the wave plate 76, the spacer 80, the second lens 82, the diaphragm housing 84 and the diaphragm 32 may be disposed along a first longitudinal axis "z". The first prism 72, the second prism 108, and the beam splitter 66 may be disposed along a second longitudinal axis "x". The beam splitter 66 may be disposed between the first prism 72 and the second prism 108 along the second longitudinal axis "x". The second longitudinal axis "x" may be orthogonal to the first longitudinal axis "z". The reference detector 54, the light source 50 and the signal detector 56 may be disposed along a third longitudinal axis "x'". The third longitudinal axis "x'" may be parallel to the second longitudinal axis "x" and orthogonal to the first longitudinal axis "z". The gate 110 and the temperature sensor 58 may also be disposed along the third longitudinal axis "x'", or they may disposed along another longitudinal axis which is parallel to the third longitudinal axis "x'". Although the optical components discussed in this configuration are arranged in the configuration discussed above, it is contemplated that the optical components may be arranged in any manner within the sensor 48.

Referring back now to FIG. 8, in an exemplary use and implantation of the sensor 48, the diaphragm 32 may be inserted inside the wall of a blood vessel so that the diaphragm 32 is in contact with blood in the blood vessel. The diaphragm 32 may become coated with protein, connective tissue, and endothelial cells within hours after implantation into the vessel wall tissue. The diaphragm 32 may deflect in response to blood pressure within the blood vessel each time the pressure changes within the vessel to provide real time blood pressure waveform monitoring.

In this configuration, the light source 50 is a VCSEL and emits coherent light toward the first lens 64. The first lens 64 receives light from the light source 50 and collimates the light into a collimated light 114. The collimated light 114 travels toward the beam splitter 66 where it is split into the first beam of light 68 and the second beam of light 70 which may have orthogonal linear polarizations.

The first beam of light 68 travels in a direction that is orthogonal to the direction of the second beam of light 70 where it is refracted by the first prism 72 into the refracted first beam of light 74. The refracted first beam of light 74 is directed toward the reference detector 54 where the intensity of the refracted first beam of light 74 is measured and correlated by the processing circuitry 60 into a reference light measurement.

The wave plate 76 receives the second beam of light 70 from the beam splitter 66 and modifies the linear polarization of the second beam of light 70 into the circularly polarized second beam of light 78. The wave plate 76 directs the circularly polarized second beam of light 78 toward the spacer 80 and the second lens 82 where the circularly polarized second beam of light 78 is further focused into a further focused circularly polarized second beam of light 86. The further focused circularly polarized second beam of light 86 may have a focal point disposed between the second lens 82 and the diaphragm 32. In one configuration, the focal point may be disposed in a range of 1-100 um away from the diaphragm 32. The diaphragm 32 reflects the further focused circularly polarized second beam of light 86 into a reflected diverging circularly polarized second beam of light 116. The diaphragm 32 deflects to define a concavity that may increase or decrease the distance of the apex of the diaphragm 32 from the focal point of the focused circularly polarized second beam of light 116 depending upon the pressure in the blood vessel. The reflected diverging circularly polarized second beam of light 116 is reflected by the diaphragm 32 toward the second lens 82 and the second lens 82 may capture at least a portion of the reflected diverging circularly polarized second beam of light 116 depending upon the location of the apex of the diaphragm 32. The second lens 82 may re-focus the reflected diverging circularly polarized second beam of light 116 into a reflected focused circularly polarized second beam of light 118. The reflected focused circularly polarized second beam of light 118 may pass through the spacer 80 and the wave plate 76. The wave plate 76 may convert the polarization of the reflected focused circularly polarized second beam of light 118 into a linear polarization which is orthogonal to the polarization of the second beam of light 70 to a reflected focused linearly polarized second beam of light 120. The beam splitter 60 directs the reflected focused linearly polarized second beam of light 120 into the second prism 108 and the second prism 108 refracts the reflected focused linearly polarized second beam of light 120 into the third beam of light 122 and directs it toward the aperture 112 in the gate 110.

The signal detector 56 then detects the portion of the third beam of light 77 that is passed through the aperture 112 and measures the light properties. The light measurement measured by the signal detector 56 is compared against the reference light measurement made by the reference detector 54. The comparison may then correlated by processing circuitry 60 into a blood pressure waveform measurement in real-time. The signal detector 56 and the reference detector 54 may measure changes in light intensity, an area of light which is in contact with the signal detector 56 or the reference detector 54, and light wavelength.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A confocal displacement sensor, comprising:
   a light source configured to emit light;
   a first lens, the first lens being configured to focus the light emitted from the light source;
   a beam splitter, the beam splitter being configured to receive the focused light from the first lens and split the focused light into a first beam of light and a second beam of light;
   a first prism, the first prism being configured to refract light from the first beam of light;
   a reference detector, the reference detector being configured to receive the refracted first beam of light from the first prism;
   a wave plate, the wave plate being configured to receive the second beam of light from the beam splitter;
   a second lens, the second lens being configured to further focus the second beam of light from the wave plate;
   a diaphragm housing, the diaphragm housing having a first portion, a second portion, and a lumen there through, the first portion of the diaphragm housing having a first length and the second portion of the diaphragm housing having a second length, the second length being longer than the first length, the first portion of the diaphragm housing having a first diameter and the second portion of the diaphragm housing having a second diameter, the first diameter being larger than the second diameter, the diaphragm housing being sized to releasably retain the second lens inside the lumen;
   a diaphragm, the diaphragm being configured to reflect light from the further focused second beam of light, the diaphragm being disposed at the distal end of the second portion of the diaphragm housing to seal the lumen, the diaphragm housing and the diaphragm being a molded unitary piece, the diaphragm being deflectable in response to blood pressure in the range between 0 mmHg to at least 250 mmHg;
   a second prism, the second prism being configured to refract light, the beam splitter being configured to receive the reflected second beam of light from the diaphragm and then direct the second beam of light from the diaphragm to the second prism, the second prism refracting the second beam of light from the diaphragm into a third beam of light;
   a signal detector, the signal detector being configured to receive the third beam of light from the second prism and measure at least one property of light of the third beam of light; the light source, the first lens, the beam splitter, the wave plate, the second lens, the diaphragm housing, and the diaphragm being disposed along a first longitudinal axis;

the first prism, the beam splitter, and the second prism being disposed along a second longitudinal axis, the second longitudinal axis being orthogonal to the first longitudinal axis; and the reference detector and the signal detector being disposed along a third longitudinal axis, the third longitudinal axis being parallel to the second longitudinal axis and being orthogonal to the first longitudinal axis.

* * * * *